(12) United States Patent
Watanabe et al.

(10) Patent No.: US 9,382,528 B2
(45) Date of Patent: Jul. 5, 2016

(54) NITRILE HYDRATASE

(71) Applicant: Mitsubishi Rayon Co., Ltd., Chiyoda-ku (JP)

(72) Inventors: Fumiaki Watanabe, Kanagawa (JP); Takanori Ambo, Aichi (JP); Ai Hara, Kanagawa (JP)

(73) Assignee: Mitsubishi Rayon Co., Ltd., Chiyoda-ku (JP)

( * ) Notice: Subject to any disclaimer, the term of this patent is extended or adjusted under 35 U.S.C. 154(b) by 0 days.

(21) Appl. No.: 14/689,955

(22) Filed: Apr. 17, 2015

(65) Prior Publication Data

US 2015/0337287 A1 Nov. 26, 2015

Related U.S. Application Data

(62) Division of application No. 14/123,171, filed as application No. PCT/JP2012/003560 on May 30, 2012.

(30) Foreign Application Priority Data

May 31, 2011 (JP) .................................. 2011-121251

(51) Int. Cl.
*C12N 15/52* (2006.01)
*C12N 15/63* (2006.01)
(Continued)

(52) U.S. Cl.
CPC . *C12N 9/88* (2013.01); *C12P 13/02* (2013.01); *C12Y 402/01084* (2013.01); *Y02P 20/52* (2015.11)

(58) Field of Classification Search
None
See application file for complete search history.

(56) References Cited

U.S. PATENT DOCUMENTS 5,731,176 A   3/1998   Yamada et al.
5,807,730 A   9/1998   Ito et al.
(Continued)

FOREIGN PATENT DOCUMENTS

JP   9 248188    9/1997
JP   9 275978    10/1997
(Continued)

OTHER PUBLICATIONS

Lu, J., et al., "Motif CXCC in nitrile hydratase activator is critical for NHase biogenesis in vivo", FEBS Letters, vol. 553, No. 3, pp. 391-396,( 2003).
(Continued)

*Primary Examiner* — Manjunath Rao
*Assistant Examiner* — William W Moore
(74) *Attorney, Agent, or Firm* — Oblon, McClelland, Maier & Neustadt, L.L.P.

(57) ABSTRACT

Improving wild nitrile hydratase enables the provision of a protein which has nitrile hydratase activity and which has further improved heat resistance, amide compound resistance and high temperature accumulation properties. Use protein (A) or (B), (A) being a protein characterised by having nitrile hydratase activity and by including an amino acid sequence in which a specific amino acid residue in an amino acid sequence in wild nitrile hydratase has been substituted by another amino acid residue, and (B) being a protein characterised by having nitrile hydratase activity and by including an amino acid sequence in which one or several amino acid residues in the amino acid sequence of protein (A), other than the abovementioned specific amino acid residue, is deleted, substituted and/or added.

7 Claims, 5 Drawing Sheets

(51) Int. Cl.
 C12N 9/88 (2006.01)
 C12P 13/02 (2006.01)

(56) References Cited

U.S. PATENT DOCUMENTS

| | | | |
|---|---|---|---|
| 5,827,699 | A | 10/1998 | Yanenko et al. |
| 7,288,402 | B2 | 10/2007 | Osswald et al. |
| 2001/0044141 | A1 | 11/2001 | Akoi et al. |
| 2007/0009985 | A1 | 1/2007 | Yamaki et al. |
| 2007/0065916 | A1 | 3/2007 | Payne et al. |
| 2007/0231868 | A1 | 10/2007 | Watanabe et al. |

FOREIGN PATENT DOCUMENTS

| | | |
|---|---|---|
| JP | 10 337185 | 12/1998 |
| JP | 3162091 | 2/2001 |
| JP | 2001 292772 | 10/2001 |
| JP | 2004 215513 | 8/2004 |
| JP | 2004 222538 | 8/2004 |
| JP | 2005 116206 | 12/2005 |
| JP | 2007 143409 | 6/2007 |
| JP | 2008 253182 | 10/2008 |
| JP | 2010 172295 | 8/2010 |
| WO | 2004 056990 | 7/2004 |

OTHER PUBLICATIONS

Piersma, S.R., et al., "Arginine 56 Mutation in the beta subunit of nitrile hydratase: importance of hydrogen bonding to the non-heme iron center", Journal of Inorganic Biochemistry, vol. 80, No. 3-4, pp. 283-288, (2000).

Yamanaka, Y. et al., "Kinetic and structural studies on roles of the serine ligand and a strictly conserved tyrosine residue in nitrile hydratase", Journal of Biological Inorganic Chemistry, vol. 15, No. 5, pp. 655-665, (2010).

Hashimoto, Y. et al., "Site-directed mutagenesis for cysteine residues of cobalt-containing nitrile hydratase", Journal of Inorganic Biochemistry, vol. 91, No. 1, pp. 70-77, (2002).

Heald, S.C., et al., "Physiology, biochemistry and taxonomy of deep-sea nitrile metabolising Rhodococcus strains", Antonie Van Leeuwenhoek, vol. 80, pp. 169-183, (2001).

"R2 Molecular Cloning, A Laboratory Manual $2^{nd}$ edition", Cold Spring Harbor Laboratory Press, total pages 10, (1989).

"Directed Mutagenesis Using the Polymerase Chain Reaction", Current Protocols in Molecular Biology, John Wiley & Sons (1987-1997) pp. 8.5.1-8.5.10, (1997).

International Search Report Issued Sep. 11, 2012 in PCT/JP12/003560 Filed May 30, 2012.

Kobayashi, M., et al., "Cloning, nucleotide sequence and expression in *Escherichia coli* of two cobalt-containing nitrile hydratase genes from Rhodococcus rhodochrous J1," Biochimica Et Biophysica Acta, vol. 1129, No. 1, 1991, pp. 23-33.

Office Action issued May 6, 2015 in co-pending U.S. Appl. No. 14/123,171.

Takakazu Kaneko et al., "Complete Genomic Sequence of Nitrogen-fixing Symbiotic Bacterium *Bradyrhizobium japonicum* USDA110", DNA Research, 2002, vol. 9, pp. 189-197.

Steven D. Brown. et al., "Draft Genome Sequence of *Rhizobium* sp. Strain PDO1-076, a Bacterium Isolated from *Populus deltoides*", Journal of Bacteriology, Apr. 2012, vol. 194, pp. 2383-2384.

U.S. Office Action dated Dec. 2, 2015, in co-pending U.S. Appl. No. 14/123,171.

FIG.2-1

Alignment results of β-subunit

```
Rhocococcus J1-H           1:MDGIHDTGGMTGYGPVPYQKDEPFFHYEWEGRTLSILTWMHLKGISWWDKSRFFRESMGN  60
Rhodococcus MS             1:MDGIHDTGGMTGYGPVPYQKDEPFFHYEWEGRTLSILTWMHLKGMSWWDKSRFFRESMGN  60
Rhodococcus ruber TH       1:MDGIHDTGGMTGYGPVPYQKDEPFFHYEWEGRTLSILTWMHLKGMSWWDKSRFFRESMGN  60
R. pyridinovorans MW3      1:MDGIHGTGGMTGYGPVPYQKDEPFFHYEWEGRTLSILTWMHLKGISWWDKSRFFRESMGN  60
R. pyridinovorans S85-2    1:MDGIHDTGGMTGYGPVPYQKDEPFFHYEWEGRTLSILTWMHLKGISWWDKSRFFRESMGN  60
R. pyridinovorans MS-38    1:MDGIHDTGGMTGYGPVPYQKDEPFFHYEWEGRTLSILTWMHLKGISWWDKSRFFRESMGN  60
Nocardia sp JBRs           1:MDGIHDTGGMTGYGPVPYQKDEPFFHYEWEGRTLSILTWMHLKGISWWDKSRFFRESMGN  60
Nocardia YS-2002           1:MDGIHDTGGMTGYGPVPYQKDEPFFHYEWEGRTLSILTWMHLKGMSWWDKSRFFRESMGN  60
R. rhodocrous ATCC39384    1:MDGIHDTGGMTGYGPVPYQKDEPFFHYEWEGRTLSILTWMELKGMSWWDKSRFFRESMGN  60
uncultured bacterium SP1   1:MDGIHDTGGMTGYGPVPYQKDEPFFHYEWEGRTLSILTWMHLKGISWWDKPRFFRESMGN  60
uncultured bacterium BD2   1:MDGIHDTGGMTGYGPVPYQKDEPFFHYEWEGRTLSILTWMHLKGISWWDKSRFFRESMGN  60
Comamonas testosteroni     1:MNGIHDTGGAHGYGPVYREPNEPVFRYDWEKTVMSLFPALFANGNFNLDEPRHGIERMNP  60
G. thermoglucosidasius Q6  1:MNGPHDLGGKRDFGPIIKHDQEPLFHEEWEAKVLAMHFALLGQGVINWDEFRHGIERMGY  60
P. thermophila JCM3095     1:MNGVYDVGGTDGLGPINRPADEPVFRAEWEKVAFAMFPATFRAGFMGLDEFRFGIEQMNP  60
R. rhodocrous Cr4          1:MDGIHDLGGRAGLGPVNPEPGEPVFHSRWERSVLTMFPAMALAGAFNLDQFRGAMEQIPP  60
                             *.*...**....**......**.*...**.............*....*..*...*....

Rhocococcus J1-H          61:ENYVNEIRNSYYTHWLSAAERILVADKIITEEERKHRVQ---EILEGRYTDRKPSRKFDP 117
Rhodococcus MS            61:ENYVNEIRNSYYTHWLSAAERILVADKIITEEERKHRVQ---EILEGRYTDRNPSRKFDP 117
Rhodococcus ruber TH      61:ENYVNEIRNSYYTHWLSAAERILVADKIITEEERKHRVQ---EILEGRYTDRNPSRKFDP 117
R. pyridinovorans MW3     61:ENYVNEIRNSYYTHWLSAAERILVADKIITEEERKHRVQ---EILEGRYTDRKPSRKFDP 117
R. pyridinovorans S85-2   61:ENYVNEIRNSYYTHWLSAAERILVADKIITEEERKHRVQ---EILEGRYTDRKPSRKFDP 117
R. pyridinovorans MS-38   61:ENYVNEIRNSYYTHWLSAAERILVADKIITEEERKHRVQ---EILEGRYTDRKPSRKFDP 117
Nocardia sp JBRs          61:ENYVNEIRNSYYTHWLSAAERILVADKIITEEERKHRVQ---EILEGRYTDRNPSRKFDP 117
Nocardia YS-2002          61:ENYVNEIRNSYYTHWLSAAERILVADKIITEEERKHRVQ---EILEGRYTDRNPSRKFDP 117
R. rhodocrous ATCC39384   61:ENYVNEIRNSYYTHWLSAAERILVADKIITEEERKHRVQ---EILEGRYTDRNPSRKFDP 117
uncultured bacterium SP1  61:ENYVNEIRNSYYTHWLSAAERILVADKIITEEERKHRVQ---EILEGRYTDRKPSRKFDP 117
uncultured bacterium BD2  61:ENYVDEIRNSYYTHWLSAAERILVADKIITEEERKHRVQ---EILEGRYTDRKPSRKFDP 117
Comamonas testosteroni    61:IDY---LKGTYYEHWIHSIETLLVEKGVLTATEL--------ATGKASGKTATPVLTP  107
G. thermoglucosidasius Q6 61:VYY---LTSSYYEHWLASLETVLAEKNIINSEQYRKRIR---EIEYGMSVPVSEKPELKE 114
P. thermophila JCM3095    61:AEY---LESPYYWHWIRTYIHHGVRTGKIDLEELERRTQYVRENPDAPLPEHEQKPELI- 116
R. rhodocrous Cr4         61:HDY---LTSQYYEHWMHAMIHYGIEAGIFDPNELDRRTQYYLEHPDED-PPLRQDPQLV- 115
                            ..*........**.**........................   .............

Rhocococcus J1-H         118:AQIEKAIERLHEPHSLALPGAEPSFSLGDKIKVKSM-NPLGHTRCPKYVRNKIGEIVAYH 176
Rhodococcus MS           118:AEIEKAIERLHEPHSLALPGAEPSFSLGDKVKVKNM-NPLGHTRCPKYVRNKIGEIVTSH 176
Rhodococcus ruber TH     118:AEIEKAIERLHEPHSLALPGAEPSFSLGDKVKVKNM-NPLGHTRCPKYVRSKIGEIVTSH 176
R. pyridinovorans MW3    118:AQIEKAIERLHEPHSLALPGAEPSFSLGDKIKVKSM-NPLEHTRCPKYVRNKIGEIVTYH 176
R. pyridinovorans S85-2  118:AQIEKAIERLHEPHSLALPGAEPSFSLGDKIKVKSM-NPLGHTRCPKYVRNKIGEIVTYH 176
R. pyridinovorans MS-38  118:AQIEKAIERLHEPHSLALPGAEPSFSLGDKIKVKSM-NPLGHTRCPKYVRNKIGEIVTYH 176
Nocardia sp JBRs         118:AEIEKAIERLHEPHSLALPGAEPSFSLGDKVKVKNM-NPLGHTRCPKYVRNKIGEIVTSH 176
Nocardia YS-2002         118:AEIEKAIERLHEPHSLALPGAEPSFSLGDKVKVKNM-NPLGHTRCPKYVRNKIGEIVTSH 176
R. rhodocrous ATCC39384  118:AEIEKAIERLHEPHSLVLPGAEPSFSLGDKVKVKNM-NPLGHTRCPKYVRNRIGEIVTSH 176
uncultured bacterium SP1 118:AQIEKAIERLHEPHSLALPGAEPSFSLGDKIKVKSM-NPLGHTRCPKYVRNKIGEIVAYH 176
uncultured bacterium BD2 118:AQIEKAIERLHEPHSLALPGAEPSFSLGDKNQSEEY-EPAGTHTVPEICA---------  166
Comamonas testosteroni   108:AIVDGLLSTG--ASAAREEGAKARFAVGDKVRVLNK-NPVGHTRMPRYTRGKVGTVVIDH 164
G. thermoglucosidasius Q6 115:SLLSEVIYGTKISSERRESTVSPRFRPGDRVRVKHF-YTNKHTRCPQYVMGKVGVVELLH 173
P. thermophila JCM3095   117:EFVNQAVYGG--LPASREVDRPPKFKEGD-VVRFSTASPKGHARRARYVRGKTGTVVKHH 173
R. rhodocrous Cr4        116:ETLSQLIMHG---ADYRRPTDAEGVFAVGDKVVVRSDASPNTHTRRAGYIRGRTGEIVAH 173
                            ....................*..**.**........ ...............
```

FIG.2-2

Alignment results of β-subunit (continuation of Fig. 2-1)

```
Rhocococcus J1-H          177:GCQ-IYPESSSAG-LGDDPRPLYTVAFSAQELWGDD-GNGKDVVCVDLWEPYLISA---- 229
Rhodococcus M8            177:GCQ-IYPESSSAG-LGDDPRPLYTVAFSAQELWGDD-GNGKDVVCVDLWEPYLISA---- 229
Rhodococcus ruber TH      177:GCQ-IYPESSSAG-LGDDPRPLYTVAFSAQELWGDD-GNGKDVVCVDLWEPYLISA---- 229
R. pyridinovorans MW3     177:GCQ-IYPESSSAG-LGDDPRPLYTVAFSAQELWGDD-GNGKDVVCVDLWEPYLISA---- 229
R. pyridinovorans S85-2   177:GCQ-IYPESSSAG-LGDDPRPLYTVAFSAQELWGDD-GNGKDVVCVDLWEPYLISA---- 229
R. pyridinovorans MS-38   177:GCQ-IYPESSSAG-LGDDPRPLYTVAFSAQELWGDD-GNGKDVVCVDLWEPYLISA---- 229
Nocardia sp JBRs          177:GCQ-IYPESSSAG-LGDDPRPLYTVAFSAQELWGDD-GNGKDVVCVDLWEPYLISA---- 229
Nocardia YS-2002          177:GCQ-IYPESSSAG-LGDDPRPLYTVAFSAQELWGDD-GNGKDVVCVDLWEPYLISA---- 229
R. rhodocrous ATCC39384   177:GCQ-IYPESSSAG-LGDDPRPLYTVAFSAQELWGDD-GNGKDVVCVDLWEPYLISA---- 229
uncultured bacterium SP1  177:GCQ-IYPESSSAG-LGDDPRP-------------------------------------- 195
uncultured bacterium BD2  166:----------------------------------------------------------- 166
Comamonas testosteroni    165:GVF-VTPDTAAHG-KGEHPQHVYTVSFTSVELWGQDASSPKDTIRVDLWDDYLEPA---- 218
G. thermoglucosidasius Q6 174:GNH-VFPDSNAHG-DGEAPQPLYNVRFEARELWGGE-AHEKDSLNLDLWDSYLTHA---- 226
P. thermophila JCM3095    174:GAY-IYPDTAGNG-LGECPEHLYTVRFTAQELWGPE-GDPNSSVYYDCWEPYIELVDTKA 230
R. rhodocrous Cr4         174:GAY-VFPDTNAVG-AGEHPEHLYTVRFSATELWGET-ATSNAVNHIDVFEPYLLPA---- 226
                                ... ..........  ....................... ....................

Rhocococcus J1-H          229:----                                                        229
Rhodococcus M8            229:----                                                        229
Rhodococcus ruber TH      229:----                                                        229
R. pyridinovorans MW3     229:----                                                        229
R. pyridinovorans S85-2   229:----                                                        229
R. pyridinovorans MS-38   229:----                                                        229
Nocardia sp JBRs          229:----                                                        229
Nocardia YS-2002          229:----                                                        229
R. rhodocrous ATCC39384   229:----                                                        229
uncultured bacterium SP1  195:----                                                        195
uncultured bacterium BD2  166:----                                                        166
Comamonas testosteroni    218:----                                                        218
G. thermoglucosidasius Q6 226:----                                                        226
P. thermophila JCM3095    231:AAA-                                                        233
R. rhodocrous Cr4         226:----                                                        226
```

FIG.3-1

Alignment results of α-subunit

```
Rhocococcus J1-H                 1:----------------MSEHVNKYTEYEARTKAIETLLYERGLITPAAVDRVVSYYENEIGPMG  48
R. rhodocrous M8                 1:----------------MSEHVNKYTEYEARTKAIETLLYERGLITPAAVDRVVSYYENEIGPMG  48
R. ruber TH                      1:----------------MSEHVNKYTEYEARTKAIETLLYERGLITPAAVDRVVSYYENEIGPMG  48
Rhodococcus_pyridinivorans_MW3   1:----------------MSEHVNKYTEYEARTKAIETLLYERGLITPAAVDRVVSYYENEIGPMG  48
Rhodococcus pyridinivorans S85-2 1:----------------MSEHVNKYTEYEARTKAIETLLYERGLITPAAVDRVVSYYENEIGPMG  48
Nocardia_JBRs                    1:----------------MSEHVNKYTEYEARTKAIETLLYERGLITPAAVDRVVSYYENEIGPMG  48
Nocardia_sp_YS-2002              1:----------------MSEHVNKYTEYEARTKAIETLLYERGLITPAAVDRVVSYYENEIGPMG  48
uncultured bacterium BD2         1:----------------MSEHVNKYTEYEARTKAIETLLYERGLITPAAVDRVVSYYENEIGPMG  48
uncultured bacterium SP1         1:----------------MSEHVNKYTEYEARTKAVETLLYERGLITPAAVDRVVSYYENEIGPMG  48
R. rhodocrou ATCC39484           1:---------------VSEHVNKYTEYEARTKAIETLLYERGLITPAAVDRVVSYYENEIGPMG  48
Sinorhizobium medicae WSM419     1:MSEHRHGPGEEHGHHHDNHLTDMEARVKALETVLTEKGLIDPAAIDAIVDTYETKVGPRN     60
P. thermophila JCM3095           1:-------MTENILRKSDEEIQKEITARVKALESMLIEQGILTTSMIDRMAEIYENEVGPHL    54
R. rhodocrous Cr4                1:--------MTAHNPVQGTFPRSNEEIAARVKAMEAILVDKGLISTDAIDYMSSVYENEVGPQL  55
                                                 **.**.*..*..*........*.....**...**..

Rhocococcus J1-H                 49:GAKVVAKSWVDPEYRKWLEEDATAAMASLGYAGEQAHQISAVFNDSQTHHVV VCTLCSCY 108
R. rhodocrous M8                 49:GAKVVAKSWVDPEYRKWLEEDATAAMASLGYAGEQAHQISAVFNDSQTHHVV VCTLCSCY 108
R. ruber TH                      49:GAKVVAKSWVDPEYRKWLEEDATAAMASLGYAGEQAHQISAVFNDSQTHHVV VCTLCSCY 108
Rhodococcus_pyridinivorans_MW3   49:GAKVVAKSWVDPEYRKWLEEDATAAMASLGYAGEQAHQISAVFNDSQTHHVV VCTLCSCY 108
Rhodococcus pyridinivorans S85-2 49:GAKVVAKSWVDPEYRKWLEEDATAAMASLGYAGEQAHQISAVFNDSQTHHVV VCTLCSCY 108
Nocardia_JBRs                    49:GAKVVAKSWVDPEYRKWLEEDATAAMASLGYAGEQAHQISAVFNDSQTHHVV VCTLCSCY 108
Nocardia_sp_YS-2002              49:GAKVVAKSWVDPEYRKWLEEDATAAMASLGYAGEQAHQISAVFNDSQTHHVV VCTLCSCY 108
uncultured bacterium BD2         49:GAKVVAKSWVDPEYRKWLEEDATAAMASLGYAGEQAHQISAVFNDSQTHHVV VCTLCSCY 108
uncultured bacterium SP1         49:GAKVVAKSWVDPEYRKWLEEDATAAMASLGYAGEQA-------------HHVV VCTLCSCY  96
R. rhodocrou ATCC39484           49:GAKVVAKSWVDPEYRKWLEEDATAAMASLGYAGEQAHQISAVFNDSQTHHVV VCTLCSCY 108
Sinorhizobium medicae WSM419     61:GARVVAKAWSDPDFADWLRRDATAAIASLGFTGRQGEHMRAVFNTSETHHNLIVCTLCSCY 120
P. thermophila JCM3095           55:GAKVVVKAWTDPEFKKRLLADGTEACKELGIGGLQGEDMMWVENTDEVHHVVVCTLCSCY  114
R. rhodocrous Cr4                56:GAKIAAHAWVDPEFKQRLLADATGACKEMGVGGMQGEEMVVLENTDTVNNMVVCTLCSCY  115
                                   **......*.**....*..*.*.*....*..*.*................*******

Rhocococcus J1-H                 109:PWPVLGLPPAWYKSMEYRSRVVADPRGVLKRDFGFDIPDEVEVRVWDSSSEIRYIVIPER 168
R. rhodocrous M8                 109:PWPVLGLPPAWYKSMEYRSRVVADPRGVLKRDFGFDIPDEVEVRVWDSSSEIRYIVIPER 168
R. ruber TH                      109:PWPVLGLPPAWYKSMEYRSRVVADPRGVLKRDFGFDIPDEVEVRVWDSSSEIRYIVIPER 168
Rhodococcus_pyridinivorans_MW3   109:PWPVLGLPPAWYKSMEYRSRVVADPRGVLKRDFGFDIPDEVEVRVWDSSSEIRYIVIPER 168
Rhodococcus pyridinivorans S85-2 109:PWPVLGLPPAWYKSMEYRSRVVADPRGVLKRDFGFDIPDEVEVRVWDSSSEIRYIVIPER 168
Nocardia_JBRs                    109:PWPVLGLPPAWYKSMEYRSRVVADPRGVLKRDFGFDIPDEVEVRVWDSSSEIRYIVIPER 168
Nocardia_sp_YS-2002              109:PWPVLGLPPAWYKSMEYRSRVVADPRGVLKRDFGFDIPDEVEVRVWDSSSEIRYIVIPER 168
uncultured bacterium BD2         109:PWPVLGLPPAWYKSMEYRSRVVADPRGVLKRDFGFDIPDEVEVRVWDSSSEIRYIVIPER 168
uncultured bacterium SP1          97:PWPVLGLPPAWYKSMEYRSRVVADPRGVLKRDFGFDIPDEVEVRVWDSSSEIRYIVIPER 156
R. rhodocrou ATCC39484           109:PWPVLGLPPAWYKSMEYRSRVVADPRGVLKRDFGFDIPDEVEVRVWDSSSEIRYIVIPER 168
Sinorhizobium medicae WSM419     121:PWAVLGLPPVWYKAPPYRSRAVIDPRGVLA-EFGLNLPAEKKIRVWDSTAELRYLVVPER 179
P. thermophila JCM3095           115:PWPVLGLPPNWFKEPQYRSRVVREPRQLLKEEFGFEVPPSKEIKVWDSSSEMRFVVLPQR 174
R. rhodocrous Cr4                116:PWPVLGLPPNWYKYPAYRARAARDPRGVM-AEFGYTPASDVEIRVWDSSAELRYWVLPQR 174
                                    **.******.*.*...**.**....**......**.........****..*.*..*.*.*
```

FIG.3-2

Alignment results of α-subunit (continuation of Fig. 3-1)

```
Rhocococcus J1-H                    169:PAGTDGWSEEELTKLVSRDSMIGVSNALTPQEVIV          203
R.rhodocrous M8                     169:PAGTDGWSEDELAKLVSRDSMIGVSNALTPQEVIV          203
R.ruber TH                          169:PAGTDGWSEDELAKLVSRDSMIGVSNALTPQEVIV          203
Rhodococcus_pyridinivorans_MW3      169:PAGTDGWSEEELTKLVSRDSMIGVSNALTPQEVIV          203
Rhodococcus pyridinivorans S85-2    169:PAGTDGWSEEELTKLVSRDSMIGVSNALTPQEVIV          203
Nocardia_JBRs                       169:PAGTDGWSEDELAKLVSRDSMIGVSNALTPQEVIV          203
Nocardia_sp_YS-2002                 169:PAGTDGWSEDELAKLVSRDSMIGVSNALTPQEVIV          203
uncultured bacterium BD2            169:PAGTDGWSEEELTKLVSRDSMIGVSNALTPQEVIV          203
uncultured bacterium SP1            157:PAGTDGWSEEELTKLVSRDSIIGV-------             180
R.rhodocrou ATCC39484               169:PAGTDGWSEDELAKLVSRDSMIGVSNALTPQEVIV          203
Sinorhizobium medicae WSM419        180:PAATDDLGEDALAKLVTRDSMIGTGLALSPEAFR-         213
P.thermophila JCM3095               175:PAGTDGWSEEELATLVTRESMIGVEPAKAVA----         205
R.rhodocrous Cr4                    175:PAGTENFTEEQLAALVTRDSLIGVSVPTAPNKA--         207
                                        **.*....*..*..**.*.*.**............
```

NITRILE HYDRATASE

CROSS REFERENCE TO RELATED APPLICATIONS

The present application is a divisional of U.S. patent application Ser. No. 14/123,171, filed on Nov. 29, 2013, the text of which is incorporated by reference, which is a National Stage entry under 35 U.S.C. 371 of PCT/JP12/003560, filed on May 30, 2012 and claims priority to Japanese Patent Application No. 2011-121251, filed on May 31, 2011.

TECHNICAL FIELD

The present invention relates to an improved (mutant) nitrile hydratase and its production method. The present invention also relates to genomic DNA that encodes the enzyme, a recombinant vector containing the genomic DNA, a transformant containing the recombinant vector, and a method for producing an amide compound.

DESCRIPTION OF BACKGROUND ART

In recent years, a nitrile hydratase was found, which is an enzyme having nitrile hydrolysis activity that catalyses the hydration of a nitrile group to its corresponding amide group. Also, methods are disclosed to produce corresponding amide compounds from nitrile compounds using the enzyme or a microbial cell or the like containing the enzyme. Compared with conventional chemical synthetic methods, such methods are known by a high conversion rate or selectivity rate from a nitrile compound to a corresponding amide compound.

Examples of microorganisms that produce a nitrile hydratase are the genus Corynebacterium, genus Pseudomonas, genus Rhodococcus, genus Rhizobium, genus Klebsiella, genus Pseudonocardia and the like. Among those, Rhodococcus rhodochrous J1 strain has been used for industrial production of acrylamides, and its usefulness has been verified. Furthermore, a gene encoding a nitrile hydratase produced by the J1 strain has been identified (see patent publication 1).

Meanwhile, introduction of a mutation into a nitrile hydratase has been attempted not only as a way to use a nitrile hydratase isolated from naturally existing microorganisms or the gene of such a nitrile hydratase, but also as a way to change the activity, substrate specificity, Vmax, Km, heat stability, stability in a substrate, stability in a subsequent product and the like of a nitrile hydratase (see patent publication 2). Nitrile hydratase genes with improved heat resistance and amide-compound resistance have been produced by the inventors of the present invention (patent publications 3 and 4).

However, considering production costs such as the cost of catalysts when producing amide compounds, it is useful to develop a nitrile hydratase with further improved heat resistance and amide-compound resistance, and enhanced capability of reacting at a high temperature. Thus, obtaining enzymes with such improved properties is highly desired for the purpose of reducing the amount of enzymes needed for reactions, lowering production costs and the like.

PRIOR ART PUBLICATION

Patent Publication

Patent publication 1: Japanese patent publication 3162091
Patent publication 2: International publication pamphlet WO2004/056990
Patent publication 3: International publication pamphlet WO2005/116206
Patent publication 4: Japanese laid-open patent publication 2007-143409

SUMMARY OF THE INVENTION

Problems to be Solved by the Invention

The objective of the present invention is to improve a nitrile hydratase so as to provide a protein having an improved nitrile hydratase activity with enhanced heat resistance, amide-compound resistance and high-temperature accumulation properties. Another objective of the present invention is to provide a nitrile hydratase collected from genomic DNA encoding the protein, a recombinant vector containing the genomic DNA, a transformant containing the recombinant vector, and a culture of the transformant, as well as a method for producing such a nitrile hydratase. Yet another objective of the present invention is to provide a method for producing an amide compound using the culture or the processed product of the culture.

Solutions to the Problems

The inventors of the present invention have conducted extensive studies to solve the above problems. As a result, in the amino acid sequence of a wild-type nitrile hydratase, the inventors have found that a protein in which a specific amino-acid residue is substituted with another amino-acid residue exhibits a nitrile hydratase activity with enhanced heat resistance, amide-compound resistance and high-temperature accumulation properties. Accordingly, the present invention is accomplished.

Namely, the present invention is as follows.

(1) Protein (A) or (B) Below:
(A) A protein having nitrile hydratase activity and characterized by the following: in the amino-acid sequence of a wild-type nitrile hydratase, amino-acid residues described in (a), (b), (c), (d) and (e) below are substituted with other amino-acid residues, and at least one amino-acid residue selected from among (f)~(q) below is substituted with another amino-acid residue:
  (a) the amino-acid residue at position 167 counted downstream from the N-terminal amino-acid residue in the amino-acid sequence of the β subunit;
  (b) the amino-acid residue at position 219 counted downstream from the N-terminal amino-acid residue in the amino-acid sequence of the β subunit;
  (c) the amino-acid residue at position 57 counted downstream from the N-terminal amino-acid residue in the amino-acid sequence of the β subunit;
  (d) the amino-acid residue at position 114 counted downstream from the N-terminal amino-acid residue in the amino-acid sequence of the β subunit;
  (e) the amino-acid residue at position 107 counted downstream from the N-terminal amino-acid residue in the amino-acid sequence of the β subunit;
  (f) the amino-acid residue at position 218 counted downstream from the N-terminal amino-acid residue in the amino-acid sequence of the β subunit;
  (g) the amino-acid residue at position 190 counted downstream from the N-terminal amino-acid residue in the amino-acid sequence of the β subunit;
  (h) the amino-acid residue at position 168 counted downstream from the N-terminal amino-acid residue in the amino-acid sequence of the β subunit;

(i) the amino-acid residue at position 144 counted downstream from the N-terminal amino-acid residue in the amino-acid sequence of the β subunit;

(j) the amino-acid residue at position 133 counted downstream from the N-terminal amino-acid residue in the amino-acid sequence of the β subunit;

(k) the amino-acid residue at position 112 counted downstream from the N-terminal amino-acid residue in the amino-acid sequence of the β subunit;

(l) the amino-acid residue at position 105 counted downstream from the N-terminal amino-acid residue in the amino-acid sequence of the β subunit;

(m) the amino-acid residue at position 95 counted downstream from the N-terminal amino-acid residue in the amino-acid sequence of the β subunit;

(n) the amino-acid residue at position 17 counted downstream from the N-terminal amino-acid residue in the amino-acid sequence of the β subunit;

(o) the amino-acid residue at position 15 counted downstream from the N-terminal amino-acid residue in the amino-acid sequence of the β subunit;

(p) the amino-acid residue at position 67 counted downstream from the furthermost downstream side C residue of the amino-acid sequence C(S/T)LCSC that forms a binding site with a prosthetic molecule in the amino-acid sequence of the α subunit; and (q) the amino-acid residue at position 17 counted downstream from the furthermost downstream side C residue of the amino-acid sequence C(S/T)LCSC that forms a binding site with a prosthetic molecule in the amino-acid sequence of the α subunit.

(B) A protein having nitrile hydratase activity and characterized by the following: one or multiple amino-acid residues are deleted, substituted and/or added in the amino-acid sequence of protein (A) excluding the amino-acid residues after the above substitution.

(2) DNA encoding the protein described in (1);

(3) a recombinant vector containing the genomic DNA described in (2);

(4) a transformant containing the recombinant vector described in (3);

(5) a nitrile hydratase collected from a culture obtained by incubating the transformant described in (4);

(6) a method for producing a nitrile hydratase characterized by collecting a nitrile hydratase from the culture obtained by incubating the transformant described in (4); and (7) a method for producing an amide compound characterized by a nitrile compound being brought into contact with the protein described in (1) or with a culture or a processed product of the culture obtained by incubating the transformant described in (4).

Effects of the Invention

According to the present invention, a novel improved (mutant) nitrile hydratase is obtained with enhanced heat resistance, amide-compound resistance and high-temperature accumulation properties. The improved nitrile hydratase with further enhanced heat resistance, amide-compound resistance and high-temperature accumulation properties is very useful because it can produce amide compounds at a high yield.

BRIEF DESCRIPTION OF THE DRAWINGS

FIG. 2-1 shows amino-acid sequences for β subunits of wild-type nitrile hydratases derived from various microorganisms;

FIG. 2-2 shows amino-acid sequences for β subunits of wild-type nitrile hydratases derived from various microorganisms (continued from FIG. 2-1);

FIG. 3-1 shows amino-acid sequences for α subunits of wild-type nitrile hydratases derived from various microorganisms; and FIG. 3-2 shows amino-acid sequences for α subunits of wild-type nitrile hydratases derived from various microorganisms (continued from FIG. 3-1).

MODE TO CARRY OUT THE INVENTION

Figure 1:
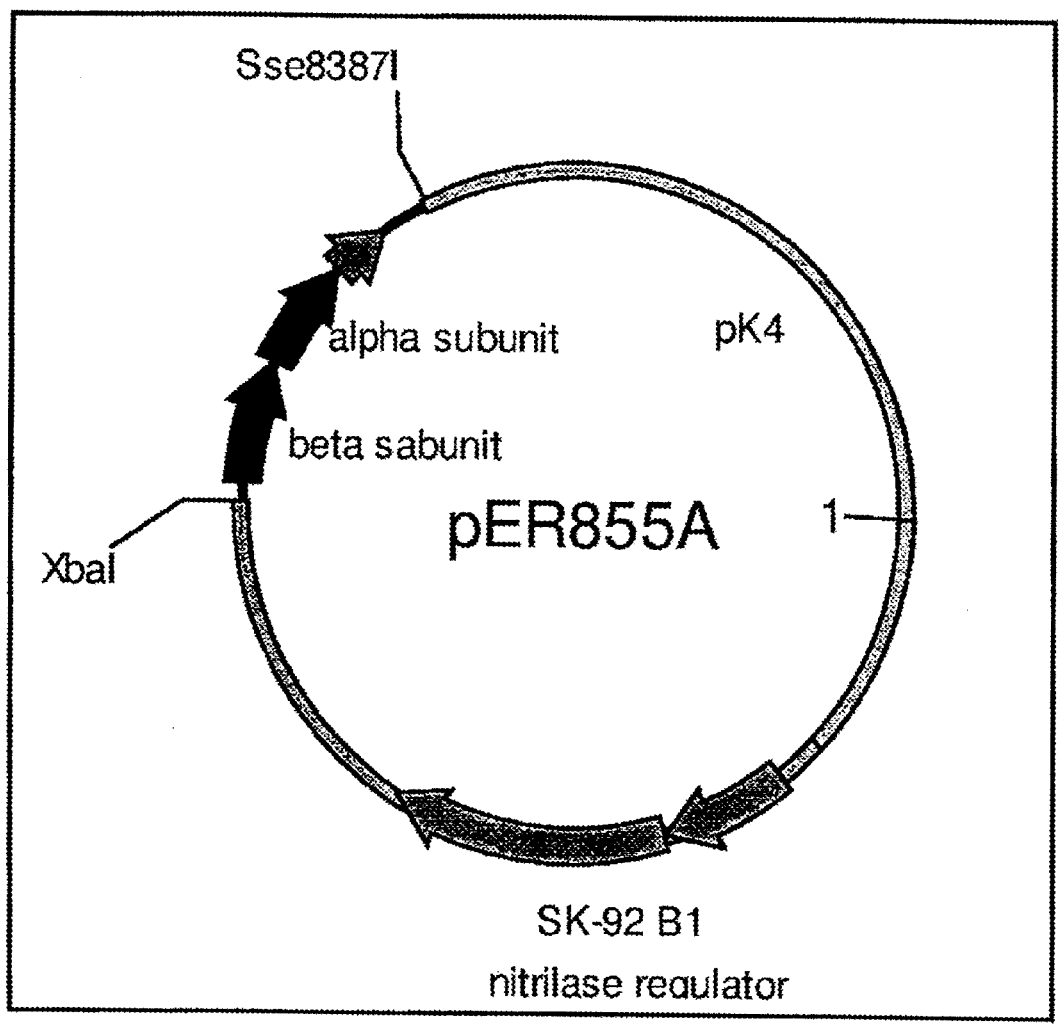
FIG. 1 is a view showing the structure of plasmid (pER855A)

In the following, the present invention is described in detail.

In the present application, unless otherwise specified, "upstream" and "upstream side" mean "N-terminal side" of an amino-acid sequence and "5' terminal side" of a base sequence.

Also, "downstream" and "downstream side" mean "C-terminal side" of an amino-acid sequence, and "3' terminal side" of a base sequence.

1. Improved Nitrile Hydratase (a) Wild-Type Nitrile Hydratase

An improved nitrile hydratase of the present invention is derived from a wild-type nitrile hydratase but is not limited to any specific wild type. Here, a "wild-type nitrile hydratase" indicates: a nitrile hydratase isolated from living organisms found in nature (microorganisms such as soil bacteria, for example); the amino-acid sequence forming the enzyme and the base sequence of the gene encoding the enzyme are not artificially deleted, inserted, or substituted by other amino acids or bases; and the nitrile hydratase retains the naturally existing original properties.

In addition to a nitrile hydratase identified to be derived from a known microorganism, a nitrile hydratase identified by a DNA sequence for which the specific origin is not known may also be included in the above "wild-type nitrile hydratase."

A "wild-type nitrile hydratase" has a higher-order structure formed with α and β subunit domains, and contains a non-heme iron atom or a non-corrin cobalt atom as a prosthetic molecule. Such a nitrile hydratase is identified and referred to as an iron-containing nitrile hydratase or a cobalt-containing nitrile hydratase.

An example of the iron-containing nitrile hydratase is derived from *Rhodococcus* N-771 strain. The conformation of such an iron-containing nitrile hydratase has been identified by X-ray crystal structural analysis. The enzyme is bonded with non-heme iron by four amino-acid residues in a cysteine cluster (SEQ ID NO: 61) forming the active site of the α subunit.

As for the cobalt-containing nitrile hydratase, examples are those derived from *Rhodococcus rhodochrous* J1 strain (hereinafter may be referred to as "J1 strain") or derived from *Pseudonocardia thermophila*. A cobalt-containing nitrile hydratase derived from the J1 strain is bonded with a cobalt atom by a site identified as a cysteine cluster (SEQ ID NO: 62) that forms the active site of the α subunit. In the cysteine cluster of a cobalt-containing nitrile hydratase derived from *Pseudonocardia thermophila*, cysteine (Cys) at position 4 from the upstream side (N-terminal side) of the cysteine cluster derived from the J1 strain is cysteine sulfinic acid (Csi), and cysteine (Cys) at position 6 counted from the furthermost downstream side (C-terminal side) is cysteine sulfenic acid (Cse).

As described above, a prosthetic molecule is bonded with a site identified as cysteine clusters "C(S/T)LCSC" (SEQ ID NO: 61 and 62) in an α subunit. Examples of a nitrile hydratase containing a binding site with such a prosthetic molecule are those that have amino-acid sequences and are encoded by genomic sequences derived from the following: *Rhodococcus rhodochrous* J1 (FERM BP-1478), *Rhodococcus rhodochrous* M8 (SU 1731814), *Rhodococcus rhodochrous* M33 (VKM Ac-1515D), *Rhodococcus rhodochrous* ATCC 39484 (JP 2001-292772), *Bacillus smithii* (JP H9-248188), *Pseudonocardia thermophila* (JP H9-275978), or *Geobacillus thermoglucosidasius*.

FIGS. 3-1 and 3-2 show the alignments of amino-acid sequences (in one-letter code) in α-subunits of wild-type nitrile hydratases derived from various microorganisms. From the top in FIGS. 3-1 and 3-2 respectively, numbers 4 and 49~60 of amino-acid sequences are shown.

On the other hand, β-subunits are thought to be attributed to structural stability. FIGS. 2-1 and 2-2 show the alignments of amino-acid sequences (in one-letter code) for β subunits of wild-type nitrile hydratases derived from various microorganisms. From the top in FIGS. 2-1 and 2-2 respectively, numbers 2 and 35~48 of amino-acid sequences are shown.

(b) Improved Nitrile Hydratase

The present invention relates to an improved (mutant) nitrile hydratase formed by substituting amino acids of a wild-type nitrile hydratase. Amino-acid sequences of wild-type nitrile hydratases to be substituted are made in public in NCBI databases such as GenBank and the like.

For example, in the α subunit derived from *Rhodococcus rhodochrous* J1 strain (FERM BP-1478), its amino-acid sequence is shown as SEQ ID NO: 4, and its base sequence is shown as SEQ ID NO: 3. Also, in the β subunit, its amino-acid sequence is shown as SEQ ID NO: 2, its base sequence is shown as SEQ ID NO: 1 and its accession number is "P21220". In addition, the accession number of the α subunit for *Rhodococcus rhodochrous* M8 (SU 1731814) is "ATT 79340" and the accession number for the β subunit is "AAT 79339." Moreover, the accession number for the α subunit derived from *Pseudonocardia thermophila* JCM 3095 is "1 IRE A" and the accession number for the β subunit is "1 IRE B."

Furthermore, also included in the scope of the present invention is an improved nitrile hydratase having nitrile hydratase activity and characterized as follows: in an amino-acid sequence in which a specific amino-acid residue is substituted, at least one amino-acid residue (for example, approximately 1~10, preferably 1~5, amino-acid residues, excluding the amino-acid residue after substitution) is deleted, substituted and/or added in the amino-acid sequence.

An "improved nitrile hydratase" of the present invention is a protein having nitrile hydratase activity and characterized as follows: in the amino-acid sequence of a wild-type nitrile hydratase, amino-acid residues identified as (a), (b), (c), (d) and (e) are substituted with other amino-acid residues, and at least one amino-acid residue selected from a group of (f)~(q) below is substituted with another amino-acid residue. Amino-acid residues identified as (d), (e), (f), (g), (h), (i), (j), (k), (l), (m), (n) (o), (p) and (q) are each preferred to be an amino-acid residue in the amino-acid sequence of a wild-type nitrile hydratase derived from a bacterium that belongs to the *Rhodococcus rhodocrous* species among various wild-type nitrile hydratases.

(a) an amino-acid residue at position 167 counted downstream from the N-terminal amino-acid residue in the amino-acid sequence of a β subunit;

(b) the amino-acid residue at position 219 counted downstream from the N-terminal amino-acid residue in the amino-acid sequence of the β subunit;

(c) the amino-acid residue at position 57 counted downstream from the N-terminal amino-acid residue in the amino-acid sequence of the β subunit;

(d) the amino-acid residue at position 114 counted downstream from the N-terminal amino-acid residue in the amino-acid sequence of the β subunit;

(e) the amino-acid residue at position 107 counted downstream from the N-terminal amino-acid residue in the amino-acid sequence of the β subunit;

(f) the amino-acid residue at position 218 counted downstream from the N-terminal amino-acid residue in the amino-acid sequence of the β subunit;

(g) the amino-acid residue at position 190 counted downstream from the N-terminal amino-acid residue in the amino-acid sequence of the β subunit;

(h) the amino-acid residue at position 168 counted downstream from the N-terminal amino-acid residue in the amino-acid sequence of the β subunit;

(i) the amino-acid residue at position 144 counted downstream from the N-terminal amino-acid residue in the amino-acid sequence of the β subunit;

(j) the amino-acid residue at position 133 counted downstream from the N-terminal amino-acid residue in the amino-acid sequence of the β subunit;

(k) the amino-acid residue at position 112 counted downstream from the N-terminal amino-acid residue in the amino-acid sequence of the β subunit;

(l) the amino-acid residue at position 105 counted downstream from the N-terminal amino-acid residue in the amino-acid sequence of the β subunit;

(m) the amino-acid residue at position 95 counted downstream from the N-terminal amino-acid residue in the amino-acid sequence of the β subunit;

(n) the amino-acid residue at position 17 counted downstream from the N-terminal amino-acid residue in the amino-acid sequence of the β subunit;

(o) the amino-acid residue at position 15 counted downstream from the N-terminal amino-acid residue in the amino-acid sequence of the β subunit;

(p) the amino-acid residue at position 67 counted downstream from the furthermost downstream side C residue of the amino-acid sequence C(S/T)LCSC that forms a binding site with a prosthetic molecule in the amino-acid sequence of the α subunit; and (q) the amino-acid residue at position 17 counted downstream from the furthermost downstream side C residue of the amino-acid sequence C(S/T)LCSC that forms a binding site with a prosthetic molecule in the amino-acid sequence of the α subunit.

Furthermore, as for the improved nitrile hydratase of the present invention, it is preferred that the amino-acid residues to be substituted in the above examples of protein be the amino-acid residues listed below.

(1) amino-acid residues identified in (a)~(e) and (n) above.
(2) amino-acid residues identified in (a)~(e) and (n) above, and at least one selected from a group of (g)~(j), (l), (m), (o) and (q);
(3) amino-acid residues identified in (a)~(e), (n), (i) and (p) above.
(4) amino-acid residues identified in (a)~(e), (n), (p) and (f) above.

(5) amino-acid residues identified in (a)~(e), (n), (i) and (p) above along with at least one amino-acid residue selected from a group of (f), (k) and (m) above.

An example of the improved nitrile hydratase of the present invention is preferred to be an enzymatic protein containing the following amino-acids in the amino-acid sequence of a wild-type nitrile hydratase derived from the J1 strain, and having nitrile hydratase activity: an amino-acid residue (asparagine) at position 167 counted from the N-terminal side in the amino-acid sequence of the β subunit; an amino-acid residue (valine) at position 219 counted from the N-terminal side in the amino-acid sequence of the β subunit; an amino-acid residue (serine) at position 57 counted from the N-terminal side in the amino-acid sequence of the β subunit; an amino-acid residue (lysine) at position 114 counted from the N-terminal side in the amino-acid sequence of the β subunit; an amino-acid residue (threonine) at position 107 counted from the N-terminal side in the amino-acid sequence of the β subunit; and an amino-acid residue (proline) at position 17 counted from the N-terminal side in the amino-acid sequence of the β subunit. Examples of code abbreviations to show such amino-acid substitutions are "Nβ167S, Vβ219A, Sβ57R, Kβ114Y, Tβ107K, Pβ17D" and the like.

Amino acids are coded by a single letter of the alphabet. The letter on the left of the numeral that shows the number of amino-acid residues existing between the terminal and the substituted position (26, for example) is a one-letter code before substitution, and the letter on the right is a one-letter code of the amino acid after substitution.

More specifically, when the amino-acid sequence of the β subunit shown as SEQ ID NO: 2 is written as "Nβ167S," it shows the amino-acid substitution performed in the improved nitrile hydratase; namely, in the amino-acid sequence of the β subunit (SEQ ID NO: 2), asparagine (N) at position 167 counted from the N-terminal amino-acid residue (including the N-terminal amino-acid residue itself) is substituted with serine (S).

Here, "α↓" means the substituted position is located downstream from the furthermost downstream C residue in the CTLCSC site (on the C-terminal side excluding the C residue itself).

Moreover, as for an improved nitrile hydra ase of the present invention, amino-acid residues to be substituted in the protein above are preferred to be those shown in Table 1.

TABLE 1

| substitution number | substitution site of amino acid | specific mode of amino-acid substitution |
|---|---|---|
| 1 | (f) | Cβ218H |
| 2 | (g) | Gβ190H |
| 3 | (h) | Kβ168R |
| 4 | (i) | Lβ144R, Lβ144S |
| 5 | (j) | Lβ133N, Lβ133R |
| 6 | (k) | Sβ112T |
| 7 | (l) | Rβ105W |
| 8 | (m) | Kβ95V |
| 9 | (n) | Pβ17D |
|   |   | Pβ17H |
|   |   | Pβ17G |
|   |   | Pβ17S |
| 10 | (o) | Pβ15S |
| 11 | (p) | Gα↓67L |
| 12 | (q) | Eα↓17S |
| 13 | (a), (b), (c), (d), (e) and (n) | Nβ167S, Vβ219A, Sβ57M, Kβ114Y, Tβ107K, Pβ17D |
| 14 | (a), (b), (c), (d), (e) and (n) | Nβ167S, Vβ219A, Sβ57M, Kβ114Y, Tβ107K, Pβ17H |
| 15 | (a), (b), (c), (d), (e) and (n) | Nβ167S, Vβ219A, Sβ57M, Kβ114Y, Tβ107K, Pβ17G |
| 16 | (a), (b), (c), (d), (e) and (n) | Nβ167S, Vβ219A, Sβ57M, Kβ114Y, Tβ107K, Pβ17S |
| 17 | (a), (b), (c), (d), (e), (n) and (l) | Nβ167S, Vβ219A, Sβ57M, Kβ114Y, Tβ107K, Pβ17S, Rβ105W |
| 18 | (a), (b), (c), (d), (e), (n) and (i) | Nβ167S, Vβ219A, Sβ57M, Kβ114Y, Tβ107K, Pβ17S, Lβ144S |
| 19 | (a), (b), (c), (d), (e), (n) and (h) | Nβ167S, Vβ219A, Sβ57M, Kβ114Y, Tβ107K, Pβ17S, Kβ168R |
| 20 | (a), (b), (c), (d), (e), (n) and (q) | Nβ167S, Vβ219A, Sβ57M, Kβ114Y, Tβ107K, Pβ17S, Eα↓17S |
| 21 | (a), (b), (c), (d), (e), (n) and (g) | Nβ167S, Vβ219A, Sβ57M, Kβ114Y, Tβ107K, Pβ17S, Gβ190H |
| 22 | (a), (b), (c), (d), (e), (n) and (m) | Nβ167S, Vβ219A, Sβ57M, Kβ114Y, Tβ107K, Pβ17S, Kβ95V |
| 23 | (a), (b), (c), (d), (e), (n) and (j) | Nβ167S, Vβ219A, Sβ57M, Kβ114Y, Tβ107K, Pβ17S, Lβ133N |
| 24 | (a), (b), (c), (d), (e), (n) and (j) | Nβ167S, Vβ219A, Sβ57M, Kβ114Y, Tβ107K, Pβ17S, Lβ133R |
| 25 | (a), (b), (c), (d), (e), (n) and (o) | Nβ167S, Vβ219A, Sβ57M, Kβ114Y, Tβ107K, Pβ17S, Pβ15S |
| 26 | (a), (b), (c), (d), (e), (n), (i) and (p) | Nβ167S, Vβ219A, Sβ57M, Kβ114Y, Tβ107K, Pβ17S, Lβ144S, Gα↓67L |
| 27 | (a), (b), (c), (d), (e), (n), (i) and (p) | Nβ167S, Vβ219A, Sβ57M, Kβ114Y, Tβ107K, Pβ17S, Lβ144S, Gα↓67V |
| 28 | (a), (b), (c), (d), (e), (n), (p) and (f) | Nβ167S, Vβ219A, Sβ57M, Kβ114Y, Tβ107K, Pβ17S, Gα↓67L, Cβ218H |

TABLE 1-continued

| substitution number | substitution site of amino acid | specific mode of amino-acid substitution |
|---|---|---|
| 29 | (a), (b), (c), (d), (e), (n), (i), (p) and (m) | Nβ167S, Vβ219A, Sβ57M, Kβ114Y, Tβ107K, Pβ17S, Lβ144S, Gα ↓ 67L, Kβ95V |
| 30 | (a), (b), (c), (d), (e), (n), (i), (p) and (k) | Nβ167S, Vβ219A, Sβ57M, Kβ114Y, Tβ107K, Pβ17S, Lβ144S, Gα ↓ 67L, Sβ112T |
| 31 | (a), (b), (c), (d), (e), (n), (i), (p) and (f) | Nβ167S, Vβ219A, Sβ57M, Kβ114Y, Tβ107K, Pβ17S, Lβ144S, Gα ↓ 67L, Cβ218H |

Among those, improved nitrile hydratases in which amino-acid residues are substituted as shown in substitution numbers 13~29 are preferred, and especially preferred are those in substitution numbers 26~29.

As for base substitutions to cause amino-acid substitutions as above, substitutions shown in Table 2 below are preferred.

TABLE 2

| amino-acid substitution | base substitution |
|---|---|
| Cβ218H | Codon "TGC" at positions 652~654 downstream (3' terminal side) from the first A of base sequence ATG (positions 1~3 in SEQ ID NO: 1) is substituted with CAT or CAC. Especially preferred to be substituted is T at position 652 downstream with C, and G at position 653 downstream with A (TGC→CAC). |
| Gβ190H | Codon "GGC" at positions 568~570 downstream (3' terminal side) from the first A of base sequence ATG (positions 1~3 in SEQ ID NO: 1) is substituted with CAT or CAC. Especially preferred to be substituted is G at position 568 downstream with C, and G at position 569 downstream with A (GGC→CAC). |
| Kβ168R | Codon "AAG" at positions 502~504 downstream (3' terminal side) from the first A of base sequence ATG (positions 1~3 in SEQ ID NO: 1) is substituted with CGT, CGC, CGA, CGG, AGA or AGG. Especially preferred to be substituted is A at position 503 downstream with G (AAG→AGG). |
| Lβ144R | Codon "CTG" at positions 258~260 downstream (3' terminal side) from the first A of base sequence ATG (positions 1~3 in SEQ ID NO: 1) is substituted with CGT, CGC, CGA, CGG, AGA or AGG. Especially preferred to be substituted is C at position 258 downstream with A, and T at position 259 downstream with G (CTG→AGG). |
| Lβ144S | Codon "CTG" at positions 430~432 downstream (3' terminal side) from the first A of base sequence ATG (positions 1~3 in SEQ ID NO: 1) is substituted with TCT, TCC, TCA, TCG, AGT or AGC. Especially preferred to be substituted is C at position 430 downstream with A, T at position 431 downstream with G, and G at position 432 downstream with C (CTG→AGC). |
| Lβ133N | Codon "CTA" at positions 397~399 downstream (3' terminal side) from the first A of base sequence ATG (positions 1~3 in SEQ ID NO: 1) is substituted with AAT or AAC. Especially preferred to be substituted is C at position 397 downstream with A, T at position 398 with A, and A at position 399 downstream with C (CTA→AAC). |
| Lβ133R | Codon "CTA" at positions 397~399 downstream (3' terminal side) from the first A of base sequence ATG (positions 1~3 in SEQ ID NO: 1) is substituted with CGT, CGC, CGA, CGG, AGA or AGG. Especially preferred to be substituted is T at position 398 downstream with G, and A at position 399 downstream with C (CTA→CGC). |
| Sβ112T | Codon "TCG" at positions 334~336 downstream (3' terminal side) from the first A of base sequence ATG (positions 1~3 in SEQ ID NO: 1) is substituted with ACT, ACC, ACA or ACG. Especially preferred to be substituted is T at position 334 downstream with A, and G at position 336 downstream with C (TCG→ACC). |
| Rβ105W | Codon "CGG" at positions 313~315 downstream (3' terminal side) from the first A of base sequence ATG (positions 1~3 in SEQ ID NO: 1) is substituted with TGG. Especially preferred to be substituted is C at position 313 downstream with T (CGG→TGG). |
| Kβ95V | Codon "AAG" at positions 283~285 downstream (3' terminal side) from the first A of base sequence ATG (positions 1~3 in SEQ ID NO: 1) is substituted with GTT, GTC, GTA or GTG. Especially preferred to be substituted is A at position 283 downstream with G, and A at position 284 downstream with T (AAG→GTG). |
| Pβ17D | Codon "CCC" at positions 49~51 downstream (3' terminal side) from the first A of base sequence ATG (positions 1~3 in SEQ ID NO: 1) is substituted with GAT or GAC. Especially preferred to be substituted is C at position 49 downstream with G, and C at position 50 downstream with A (CCC→GAC). |
| Pβ17H | Codon "CCC" at positions 49~51 downstream (3' terminal side) from the first A of base sequence ATG (positions 1~3 in SEQ ID NO: 1) is substituted with CAT or CAC. Especially preferred to be substituted is C at position 50 downstream with A (CCC→CAC). |
| Pβ17G | Codon "CCC" at positions 49~51 downstream (3' terminal side) from the first A of base sequence ATG (positions 1~3 in SEQ ID NO: 1) is substituted with GGT, GGC, GGA or GGG. Especially preferred to be substituted is C at position 49 downstream with G, C at position 50 downstream with G, C at position 50 downstream with G, and C at position 51 downstream with G (CCC→GGG). |
| Pβ17S | Codon "CCC" at positions 49~51 downstream (3' terminal side) from the first A of base sequence ATG (positions 1~3 in SEQ ID NO: 1) is substituted with TCT, TCC, TCA, TCG, AGT or AGC. Especially preferred to be substituted is C at position 49 downstream with A, and C at position 50 downstream with G (CCC→AGC). |
| Pβ15S | Codon "CCG" at positions 43~45 downstream (3' terminal side) from the first A of base sequence ATG (positions 1~3 in SEQ ID NO: 1) is substituted with TCT, TCC, TCA, TCG, AGT or AGC. Especially preferred to be substituted is C at position 43 downstream with A, and C at position 44 downstream with G (CCG→AGC). |

TABLE 2-continued

| amino-acid substitution | base substitution |
|---|---|
| Gα↓67L | Codon "GGT" at positions 199~201 downstream (toward 3' terminal) from the last C of base sequence TGCACTCTGTGTTCGTGC (positions 304~321 in SEQ ID NO: 3) is substituted with TTA, TTG, CTT, CTC, CTA or CTG. Especially preferred to be substituted is G at position 199 downstream with T, G at position 200 downstream with CTG, and T at position 201 downstream with G (GGT→TTG). |
| Gα↓67V | Codon "GGT" at positions 199~201 downstream (toward 3' terminal) from the last C of base sequence TGCACTCTGTGTTCGTGC (positions 304~321 in SEQ ID NO: 3) is substituted with GTA, GTC, GTG or GTT. Especially preferred to be substituted is G at position 200 downstream with T, and T at position 201 downstream with G (GGT→GTG). |
| Gα↓17S | Codon "GAG" at positions 49~51 downstream (toward 3' terminal) from the last C of base sequence TGCACTCTGTGTTCGTGC (positions 304~321 in SEQ ID NO: 3) is substituted with TCT, TCC, TCA, TCG, AGT or AGC. Especially preferred to be substituted is G at position 49 downstream with A, and A at position 50 downstream with G, G at position 51 downstream with C (GAG→AGC). |

In the alignment of the β-subunit of a nitrile hydratase derived from the J1 strain shown as SEQ ID NO: 2, the positions of amino acids to be substituted in the present invention include 167, 219, 57, 114, 107, 218, 190, 168, 144, 133, 112, 105, 95, 17 and 15. For example, if it is a *Pseudonocardia thermophila*, positions of amino acids to be substituted in the amino-acid sequence are 164, 216, 57, 114, 107, 215, 187, 165, 141, 129, 108, 102, 92, 17 and 15. Moreover, as for positions of amino acids to be substituted in the present invention, positions 124 and 174 of the α-subunit of the J1 strain of nitrile hydratase identified as SEQ ID NO: 4 and positions 130 and 180 of *Pseudonocardia thermophila* are also included.

Aligning the amino-acid sequence is not limited to any specific method. For example, a genomic sequence analysis software such as GENTXY (Nippon Genetics Co, Ltd.), DNASIS (Hitachi Solutions, Ltd.), or a free software CLUST-ALW or BLAST may be used. FIGS. 2-1, 2-2, 3-1 and 3-2 show the alignment results obtained by using version 7, GENETXY (default setting, Nippon Genetics Co., Ltd.)

The improved nitrile hydratase activity of the present invention shows enhanced heat resistance, amide-compound resistance and high-temperature accumulation properties compared with a wild-type nitrile hydratase activity retaining the naturally existing original characteristics.

Here, "nitrile hydratase activity" means an enzymatic activity to catalyze the hydration for converting a nitrile compound to a corresponding amide compound (RCN+ $H_2O \rightarrow RCONH_2$). Determining the activity is conducted by bringing a nitrile compound as a substrate into contact with a nitrile hydratase for conversion to a corresponding amide compound and by measuring the resultant amide compound. Any nitrile compound may be used as a substrate as long as nitrile hydratase reacts with such the compound, but acrylonitrile is preferred.

Reaction conditions are a substrate concentration of 2.5%, reaction temperature of 10° C. to 30° C. and duration of 10~30 minutes. The enzymatic reactions are terminated by adding phosphoric acid. Then, using HPLC (high-performance liquid chromatography), the produced acrylamide is analyzed to measure the amount of the amide compound.

In addition, the presence of nitrile hydratase activity is simply examined by activity staining. For example, if anthranilonitrile is used as a substrate, since anthranilamide converted by a nitrile hydratase yields fluorescent, nitrile hydratase activity is easily detected at high sensitivity (reference: Antonie Van Leeuwenhoek, 80(2): 169-183, 2001).

"Improved heat resistance" means that the remaining activity of a heat-treated improved strain is at least 10% higher than the remaining activity of the comparative example treated the same way. The method for heat treatment is to supply a liquid culture, or collected and washed bacterial-cell culture, in a container and to place the container in a heating device such as a water bath or incubator so as to maintain the temperature for a predetermined duration. At that time, to enhance the stability of the enzyme, a nitrile compound or an amide compound may be added for such heat treatment. For treatment conditions, the temperature and duration are preferred to be set in such a way that the activity of the comparative example becomes no more than 50% of that prior to the heat treatment. In particular, heat treatment is preferred to be performed in a temperature range of 50° C. to 70° C. for 5 minutes to 60 minutes. Remaining activity means the ratio of the amount of an amide compound produced by heat-treated bacterial cells for activity measurement to the amount of an amide compound produced by the same amount of untreated bacterial cells for activity measurement. Untreated bacterial cells are those in a liquid culture or collected and washed bacterial-cell culture, which are refrigerated at a temperature of 4° C. The comparative example in the present invention is a transformant into which pER855A is introduced. When a nitrile hydratase shows a remaining activity at least 10% higher than that of the comparative strain, the heat resistance of the nitrile hydratase is confirmed to be improved.

"Amino-compound resistance" means that a nitrile hydratase can maintain its activity in the presence of an amide compound. A cultured transformant containing an improved nitrile hydratase, or an improved nitrile hydratase isolated from the transformant, is analyzed in the presence of an amide compound such as acrylamide (at a high concentration of 30~50%, for example) to examine the consumption amount or consumption rate of a nitrile compound such as acrylonitrile for a substrate. When the consumption amount or consumption rate exceeds 1.01 times that of the comparative example, the nitrile hydratase is confirmed to be resistant to amide compounds.

"High-temperature accumulation properties" means that a nitrile hydratase is capable of producing acrylamide at a high concentration exceeding 35% at a reaction temperature of 20° C. or higher. Enzymatic reactions of a cultured transformant containing an improved nitrile hydratase, or an improved nitrile hydratase isolated from the transformant, are continued by adding acrylonitrile, and then the concentration of a produced acrylamide is analyzed. Acrylamide may be added while the acrylonitrile content in the reaction mixture is controlled, or may be added sequentially to continue reactions. High temperature in the present application means a reaction temperature of 20° C. or higher. When the concentration of produced acrylamide exceeds that of the comparative example, the high-temperature accumulation properties of the improved nitrile hydratase is evaluated to be enhanced.

An example of amide compounds is represented by general formula (1) below:

R—CONH$_2$ (1)

(Here, "R" is a straight-chain or branched alkyl or alkenyl group having 1~10 carbon atoms with an optional substituent, a cycloalkyl group or allyl group having 3~18 carbon atoms with an optional substituent, or a saturated or unsaturated heterocyclic group with an optional substituent.) Especially, an acrylamide is preferred to have "CH2=CH—" as "R" in the formula.

The above improved nitrile hydratase is obtained by substituting amino acids of a wild-type nitrile hydratase. For example, the improved nitrile hydratase is obtained by modifying the amino-acid sequence (SEQ ID NO: 2 and/or 4) of a nitrile hydratase derived from *Rhodococcus rhodochrous* J1 strain and by selecting a nitrile hydratase with enhanced heat resistance and/or amide-compound resistance.

*Rhodococcus rhodochrous* J1 strain is internationally registered as FERM BP-1478 at the International Patent Organism Depositary, National Institute of Advanced Industrial Science and Technology (Central 6, 1-1-1 Higashi, Tsukuba, Ibaraki), deposited Sep. 18, 1987.

In nitrile hydratases other than the J1 strain, enzymes with a highly homologous amino-acid sequence are thought to acquire enhanced heat resistance and/or amide-compound resistance through the mutation above.

As for such strains, *Bacillus smithii* (JP H09-248188), *Pseudonocardia thermophila* (JP H09-275978), *Geobacillus thermoglucosidasius* and the like are listed. Especially preferred are *Rhodococcus rhodochrous* M8 (SU 1731814) and *Rhodococcus rhodochrous* M33 (VKM Ac-1515D), in which amino-acid homology is 90% or higher (high homology enzymes are listed). *Rhodococcus rhodochrous* M33 (VKM Ac-1515D) is selected as a result of the natural mutation of the M8 strain (SU 1731814) above, and is capable of constitutive expression of nitrile hydratase, but the amino-acid sequence or genomic sequence of the nitrile hydratase itself is not modified (U.S. Pat. No. 5,827,699).

Methods for conducting amino-acid substitution on a wild-type nitrile hydratase are as follows: a bacterium having nitrile hydratase activity is brought into contact for reactions with chemicals such as hydroxyl amine or nitrous acid as a mutation source; UV rays are irradiated to induce mutation; error-prone PCR or site-directed mutagenesis is employed to introduce a mutation at random into the gene that encodes a nitrile hydratase; and the like.

(b-1) Method for Introducing Random Mutation

To study functions and characteristics of proteins using a mutant, random mutagenesis is known. Random mutagenesis is a method to introduce a random mutation to the gene encoding a specific protein so that a mutant is produced. In random mutagenesis by PCR, stringency conditions are set low during DNA amplification to introduce mutation in a base sequence (error-prone PCR).

In such an error-prone PCR method, a mutation is introduced randomly into any position of the entire DNA site to be amplified. Then, by examining the function of the obtained mutant into which a mutation was introduced randomly, information of amino acids or domains important for the specific functions of a protein is obtained.

For a nitrile hydratase as the template of error-prone PCR, the nitrile hydratase gene derived from a wild type strain or DNA obtained as an amplified product by error-prone PCR are used.

As reaction conditions for error-prone PCR, for example, a composition ratio of any one, two or three among dNTP (dGTP, dCTP, dATP or dTTP) in the reaction mix is reduced relative to another dNTP. In so setting, during the DNA synthesis, at a position that requires a dNTP whose ratio is reduced, another dNTP is more likely to be used by error, and that may lead to mutation. In addition, other preferred reaction conditions are a composition in which the amount of MgCl$_2$ and/or MnCl$_2$ in the reaction mix is increased.

(b-2) Improved Nitrile Hydratase Derived from *Rhodococcus rhodochrous* J1 Strain and its Gene An improved nitrile hydratase of the present invention includes the gene encoding a protein into which mutations shown in Table 1 are introduced.

Based on a wild-type nitrile hydratase gene, DNA that encodes such an improved nitrile hydratase is produced by site-directed mutagenesis methods described in *Molecular Cloning, A Laboratory Manual, 2nd edition*, published by Cold Spring Harbor Laboratory Press (1989), *Current Protocols in Molecular Biology*, John Wiley and Sons (1987-1997) and the like. To introduce a mutation into DNA by well-known methods such as the Kunkel method or the Gapped Duplex method, mutagenesis kits applying site-directed mutagenesis methods such as follows are used: Quick-Change™ XL Site-Directed Mutagenesis Kit (made by Stratagene), GeneTailor™ Site-Directed Mutagenesis System (made by Invitrogen Corporation), TaKaRa Site-Directed Mutagenesis System (Mutan-K, Mutan-Super Express Km and the like, made by Takara Bio Inc.) and the like.

Furthermore, a gene related to the present invention includes DNA which is hybridized under stringent conditions with a DNA made up of a base sequence complementary to the base sequence of the gene of the present invention, and which encodes a protein having nitrile hydratase activity.

Such an improved nitrile hydratase gene is obtained by introducing a mutation into a wild-type gene as described above. Alternatively, using the genomic sequence or its complementary sequence or a DNA fragment as a probe, improved nitrile hydratase gene may also be obtained from cDNA libraries and genomic libraries by employing well-known hybridization methods such as colony hybridization, plaque hybridization, Southern blot or the like. Libraries constructed by a well-known method may be used, or commercially available cDNA libraries and genomic libraries may also be used.

"Stringent conditions" are those for washing after hybridization; a salt concentration of 300~2000 mM, a temperature of 40~75° C., preferably a salt concentration of 600~900 mM, and a temperature of 65° C. For example, conditions 2×SSC at 50° C. may be employed. In addition to such a salt concentration of the buffer, temperature and the like, a person skilled in the art may set conditions for obtaining DNA that encodes a nitrile hydratase of the present invention by adding various conditions such as probe concentration, probe length and reaction time.

For detailed procedures for hybridization, *Molecular Cloning, A Laboratory Manual, 2nd edition* (Cold Spring Harbor Laboratory Press (1989)) and the like may be referred to. DNA to be hybridized includes DNA or its fragment, containing a base sequence which is at least 40%, preferably 60%, more preferably 90% or greater, homologous to the genomic DNA of the present invention.

An amino acid (amino acid after substitution) that substitutes a specific amino acid residue in the amino-acid sequence of a wild-type nitrile hydratase is not limited to any specific type, and may be selected properly as long as the polypeptide (protein) that includes the amino acid after substitution exhibits nitrile hydratase activity.

(c) Recombinant Vector, Transformant

It is necessary for a nitrile hydratase gene to be put into a vector so that nitrile hydratase is expressed in the host organism to be transformed. Examples of such vectors are plasmid DNA, bacteriophage DNA, retrotransposon DNA, artificial chromosome DNA and the like.

In addition, a host to be used in the present invention is not limited to any specific type as long as the target nitrile hydratase is expressed after the recombinant vector is introduced into the host. Examples are bacteria such as *E. coli* and *Bacillus subtilis*, yeasts, animal cells, insect cells, plant cells and the like. When *E. coli* is used as a host, an expression vector with high expression efficiency, such as expression vector pkk 233-2 with a trc promoter (made by Amersham Biosciences Corp.), pTrc 99A (made by Amersham Biosciences Corp.) or the like, is preferred.

In addition to a nitrile hydratase gene, a vector may be coupled with a promoter, terminator, enhancer, splicing signal, poly A addition signal, selection marker, ribosome binding sequence (SD sequence) or the like. Examples of selection markers are a kanamycin resistance gene, dihydrofolate reductase gene, ampicillin resistance gene, neomycin resistance gene and the like.

When a bacterium is used as a host, *Escherichia coli* may be used, for example, and a *Rhodococcus* strain such as *Rhodococcus rhodochrous* ATCC 12674, *Rhodococcus rhodochrous* ATCC 17895 and *Rhodococcus rhodochrous* ATCC 19140 may also be used. Those ATCC strains are obtained from the American type culture collection.

When *E. coli* is used as a host for producing a transformant to express a nitrile hydratase, since most of the expressed nitrile hydratases are formed as inclusion bodies and are insoluble, a transformant with low catalytic activity is obtained. On the other hand, if a *Rhodococcus* strain is used as a host, nitrile hydratase is present in the soluble fraction and a transformant with high activity is obtained. Those transformants may be selected based on purposes. However, when an improved enzyme is selected under stringent conditions, a transformant with high activity derived from a *Rhodococcus* strain is preferred.

Introducing a recombinant vector into a bacterium is not limited to any specific method as long as DNA is introduced into the bacterium. For example, a method using calcium ions, electroporation or the like may be employed.

When yeast is used as a host, examples are *Saccharomyces cerevisiae, Schizosaccharomyces pombe, Pichia pastoris* and the like. As a method for introducing a recombinant vector into yeast, it is not limited specifically as long as DNA is introduced into the yeast. For example, an electroporation method, spheroplast method, lithium acetate method or the like may be employed.

When animal cells are used as a host, monkey cells COS-7, Vero, CHO cells, mouse L cells, rat GH3 cells, human FL cells or the like may be employed. As a method for introducing a recombinant vector into an animal cell, for example, an electroporation method, calcium phosphate method, lipofection method or the like may be used.

When insect cells are used as a host, Sf9 cells, Sf21 cells and the like may be used. As a method for introducing a recombinant vector into an insect cell, for example, a calcium phosphate method, lipofection method, electroporation method or the like may be used.

When plant cells are used as a host, tobacco BY-2 cells or the like may be used. However, that is not the only option. A method for introducing a recombinant vector into a plant cell, for example, an *Agrobacterium* method, particle gun method, PEG method, electroporation method or the like may be used.

(d) Method for Producing Culture and Improved Nitrile Hydratase

An improved nitrile hydratase of the present invention is obtained by incubating the above transformant and by collecting from the obtained culture.

The present invention also relates to a method for producing an improved nitrile hydratase, and the method is characterized by collecting an improved nitrile hydratase from the culture above.

In the present invention, "culture" means culture supernatant, cultured cells, cultured bacterial cells, cell homogenates or bacterial-cell homogenates. Incubation of a transformant of the present invention is conducted by a generally used method for incubating a host. The target nitrile hydratase is accumulated in the culture.

As for a culture to incubate a transformant of the present invention, any natural or synthetic culture medium is used as long as it contains a carbon source, a nitrogen source, inorganic salts or the like for the host bacteria to assimilate, and incubation of a transformant is performed efficiently. Examples of a carbon source are carbohydrates such as glucose, galactose, fructose, sucrose, raffinose and starch; organic acids such as acetic acid and propionic acid; alcohols such as ethanol and propanol; and the like. Examples of a nitrogen source are inorganic acids such as ammonia, ammonium chloride, ammonium sulfate, ammonium acetate and ammonium phosphate; ammonium salts of organic acids; and other nitrogen-containing compounds.

In addition, peptone, yeast extract, meat extract, corn steep liquor, various amino acids or the like may also be used. Examples of minerals are monopotassium phosphate, potassium dihydrogenphosphate, magnesium phosphate, magnesium sulfate, sodium chloride, ferrous sulfate, manganese sulfate, zinc sulfate, copper sulfate, calcium carbonate and the like. Also, if necessary, a defoaming agent may be used to prevent foaming during the incubation process. Moreover, cobalt ions or iron ions as prosthetic molecules of a nitrile hydratase, or nitriles and amides as an inducer of the enzyme, may also be added to the culture.

Incubation may be conducted by adding selective pressure to prevent the vector and the target gene from being eliminated. Namely, if a selection marker is a drug-resistant gene, a corresponding chemical agent may be added; or if a selection marker is an auxotrophic complementary gene, corresponding nutrition factors may be removed.

Also, if a selection marker has a genetic assimilation trait, an equivalent assimilation factor may be added as a sole factor if necessary. For example, when *E. coli* transformed by a vector containing an ampicillin-resistant gene is incubated, ampicillin may be added as needed during the incubation process.

When incubating a transformant transformed by an expression vector containing an inducible promoter, such an inducer may be added to the culture if necessary. For example, when incubating a transformant transformed by an expression vector with a promoter inducible with isopropyl-$\beta$-D-thiogalactopyranoside (IPTG), IPTG or the like may be added to the culture. Likewise, when incubating a transformant transformed by an expression vector with a trp promoter inducible with indoleacetic acid (IAA), IAA or the like may be added to the culture.

Incubation conditions of a transformant are not limited specifically as long as the productivity of the target nitrile hydratase and growth of the host are not prohibited. Generally, conditions are preferred to be 10° C.~40° C., more preferably 20° C.~37° C., for 5~100 hours. The pH value is adjusted using inorganic or organic acid, alkaline solution or the like. If it is an *E. coli*, the pH is adjusted to be 6~9.

As for incubation methods, solid-state culture, static culture, shaking culture, aeration-agitation culture and the like may be used. When an *E. coli* transformant is incubated, it is especially preferred to use shaking culture or aeration-agitation culture (jar fermentation) under aerobic conditions.

When incubated in culture conditions above, the improved nitrile hydratase of the present invention is accumulated at a high yield in the above culture medium, namely, at least in any of culture supernatant, cell culture, bacterial-cell culture, cell homogenates or bacterial-cell homogenates.

When an improved nitrile hydratase is incubated and produced in a cell or bacterial cell, the target nitrile hydratase is collected by homogenizing the cell or bacterial cell. Cells or bacterial cells are homogenized by high-pressure treatment using a French press or homogenizer, supersonic treatment, grinding treatment using glass beads or the like, enzyme treatment using lysozyme, cellulose, pectinase and the like, freezing and thawing treatment, hypotonic solution treatment, bacteriolysis induction treatment by phage, and so on.

After the homogenization process, residues of the cell homogenates or bacterial-cell homogenates (including insoluble fractions of the cell extract) are removed if necessary. To remove residues, centrifugal or filtration methods are employed. To increase the efficiency of removing residues, a coagulant or filter aid may be used. The supernatant obtained after the removal of residues is soluble fractions of the cell extract, which are used as a crudely purified improved nitrile hydratase solution.

Also, when an improved nitrile hydratase is produced in cells or bacterial cells, it is an option to collect the cells or bacterial cells themselves by a centrifuge or membrane filtration and to use without homogenizing them.

When an improved nitrile hydratase is produced outside the cells or bacterial cells, the culture may be used as is, or the cells or bacterial cells are removed using a centrifugal or filtration method. Then, the improved nitrile hydratase is collected from the culture by being extracted through ammonium sulfate precipitation, if necessary. Furthermore, dialysis or various chromatography techniques (gel filtration, ion exchange chromatography, affinity chromatography, etc.) may be used to isolate and purify the nitrile hydratase.

To check the production yield of a nitrile hydratase obtained by incubating a transformant is not limited to using any specific method, but SDS-PAGE (polyacrylamide gel electrophoresis), nitrile hydratase activity measurements or the like may be used to determine the yield per culture, per wet or dry weight in a bacterial cell, or per crude enzymatic protein. SDS-PAGE may be conducted by a method well known by a person skilled in the art. Also, the activity described above may be applied to nitrile hydratase activity.

Without using any living cells, an improved nitrile hydratase of the present invention may be produced using a cell-free protein synthesis system.

In a cell-free protein synthesis system, a protein is produced in an artificial vessel such as a test tube using a cell extract. A cell-free protein synthesis system used in the present application includes a cell-free transcription system that synthesizes RNA using DNA as a template.

In such a case, an organism corresponding to the above host is the organism from which the cell extract is derived. Here, for the cell extract, extracts of eukaryotic or prokaryotic origin, such as the extract from wheat germ, *E. coli* and the like, may be used. Such cell extracts may be concentrated or not.

The cell extract is obtained by ultrafiltration, dialysis, polyethylene glycol (PEG) precipitation or the like. In the present invention, a commercially available kit may also be used for cell-free protein synthesis. Examples of such a kit are a reagent kit PROTEIOS™ (Toyobo), TNT™ system (Promega KK), a synthesizer PG-Mate™ (Toyobo), RTS (Roche Diagnostics) and the like.

An improved nitrile hydratase obtained by cell-free protein synthesis as described above is also purified by properly selecting a chromatography type.

2. Method for Producing Amide Compound

The improved nitrile hydratase obtained above is used as an enzymatic catalyst when producing material. For example, an amide compound is produced by bringing a nitrile compound into contact with the improved nitrile hydratase. Then, the amide compound produced upon contact is collected. Accordingly, an amide compound is produced.

The isolated and purified nitrile hydratase as described above is used as an enzymatic catalyst. In addition, a gene is introduced so as to express an improved nitrile hydratase in a proper host as described above and the culture after the host is incubated or the processed products of the culture may also be used. Processed products are, for example, incubated cells immobilized with acrylamide gel or the like, those processed by glutaraldehyde, those supported by inorganic carriers such as alumina, silica, zeolite, diatomaceous earth and the like.

Here, "contact" means that an improved nitrile hydratase and a nitrile compound are present in the same reaction system or incubation system: for example, an isolated and purified improved nitrile hydratase and a nitrile compound are mixed; a nitrile compound is added into a incubation vessel of a cell to express an improved nitrile hydratase gene; cells are incubated in the presence of a nitrile compound; a cell extract is mixed with a nitrile compound; and so on.

A nitrile compound as a substrate is selected by considering the substrate specificity of the enzyme, stability of the enzyme in the substrate and the like. As for a nitrile compound, acrylonitrile is preferred. The reaction method and the method for collecting an amide compound after the completion of reactions are properly selected depending on the characteristics of the substrate and the enzymatic catalyst.

The enzymatic catalyst is preferred to be recycled as long as its activity is not deactivated. From the viewpoint of preventing deactivation and of recycling ease, the enzymatic catalyst is preferred to be used as a processed product.

EXAMPLES

In the following, examples of the present invention are described in detail. However, present invention is not limited to those.

Example 1

Obtaining Improved Nitrile Hydratase Gene and Evaluation Thereof (1)

(1) Construction of Mutant Gene Library

The plasmid used as a template was plasmid pER855A (FIG. 1) modified from plasmid pER855 (see JP 2010-172295) as follows: in the β subunit of the amino-acid sequence (SEQ ID NO: 2), the amino-acid residue positioned at 167 downstream from the N-terminal amino-acid residue was mutated from asparagine (N) to serine (S); the amino-acid residue positioned at 219 downstream from the N-terminal amino-acid residue above was mutated from valine (V) to alanine (A); the amino-acid residue positioned at 57 downstream from the N-terminal amino-acid residue above was mutated from serine (S) to methionine (M); the amino-acid residue positioned at 114 downstream from the N-terminal amino-acid residue above was mutated from lysine (K) to tyrosine (Y); and the amino-acid residue positioned at 107 downstream from the N-terminal amino-acid residue above was mutated from threonine (T) to lysine (K).

Plasmid pSJ034 used as a vector is capable of expressing a nitrile hydratase in a *Rhodococcus* strain, and was prepared from pSJ023 using a method described in JP H10-337185. Here, pSJ023 is a transformant "*R. rhodochrous* ATCC 12674/pSJ023," and is internationally registered as FERM BP-6232 at the International Patent Organism Depositary, National Institute of Advanced Industrial Science and Technology (Central 6, 1-1-1 Higashi, Tsukuba, Ibaraki), deposited Mar. 4, 1997.

First, a mutation was introduced into the nitrile hydratase gene using the following method.

<Composition of PCR Reaction Mixture>

| | |
|---|---|
| sterile water | 20 μL |
| pER855A (1 ng/mL) | 1 μL |
| Forward primer (10 mM) | 2 μL |
| Reverse primer (10 mM) | 2 μL |
| PrimeSTAR MAX (2×) | 25 μL |
| | 50 μL |

<PCR Reaction Conditions>
(98° C. for 10 sec, 55° C. for 5 sec, 72° C. for 90 sec)×30 cycles
<Primers> Primer for Saturation Mutagenesis at β17

(SEQ ID NO: 5)
β17RM-F: ggatacggaccggtcNNStatcagaaggacgag (SEQ ID NO: 6)
β17RM-R: ctcgtccttctgataSNNgaccggtccgtatcc <Reaction Conditions>
(94° C. for 30 sec, 65° C. for 30 sec, 72° C. for 3 min)×30 cycles After the completion of PCR, 5 μL of the reaction mixture was provided for 0.7% agarose gel electrophoresis, an amplified fragment of 11 kb was confirmed, and 1 μL of DpnI (provided with the kit) was added to the PCR reaction mixture, which was then reacted at 37° C. for an hour. Accordingly, the plasmid template was removed. After that, the reaction mixture was purified using Wizard SV Gel and PCR Clean-Up System (Promega KK), and transformation was introduced into JM109 by the purified PCR reaction product. A few thousand obtained colonies were collected from the plate, and plasmid DNA was extracted using QIAprep Spin Miniprep Kit (Qiagen) to construct a mutant-gene library.

(2) Producing *Rhodococcus* Transformant

The cells of *Rhodococcus rhodochrous* strain ATCC 12674 at a logarithmic growth phase were collected by a centrifugal separator, washed with ice-cooled sterile water three times and suspended in the sterile water. Then, 1 μL of plasmid prepared in (1) above and 10 μL of the bacterial-cell suspension were mixed and ice-cooled. The plasmid DNA and the bacterial-cell suspension were supplied into a cuvette, and electric pulse treatment was conducted at 2.0 KV and 200Ω using an electroporation device, Gene Pulser II (Bio-Rad Laboratories, Inc.).

The cuvette with the mixture processed by electric pulses was let stand for 10 minutes under ice-cold conditions, and a heat-shock treatment was conducted at 37° C. for 10 minutes.

Then, 500 μL of an MYK culture medium (0.5% polypeptone, 0.3% Bacto yeast extract, 0.3% Bacto malt extract, 0.2% K₂HPO₄, 0.2% KH₂PO₄) was added and let stand at 30° C. for 5 hours, and the strain was applied onto an MYK agar medium containing 50 μg/mL kanamycin. The colony obtained after incubating at 30° C. for 3 days was used as a transformant. In the same manner, transformant pER855A was prepared as a comparative strain.

(3) Amide Treatment on *Rhodococcus* Transformant

The *Rhodococcus* transformant containing a nitrile hydratase gene obtained in (2) above and ATCC 12674/pER855A as a comparative strain were used for screening. In a 96-hole deep-well plate, 1 mL each of a GGPK culture medium (1.5% glucose, 1% sodium glutamate, 0.1% yeast extract, 0.05% K₂HPO₄, 0.05% KH₂P O₄, 0.05% MgSO₄.7H₂O, 1% CoCl₂, 0.1% urea, 50 μg/mL kanamycin, pH at 7.2) was supplied. In each culture medium, the above strain was inoculated, and liquid culture was carried out at 30° C. for 3 days.

Next, 30 μL of the liquid culture obtained above was dispensed in a 96-hole plate and the culture medium was removed by centrifugation. Lastly, 40 μL of 50% acrylamide solution was added to suspend the bacteria. The transformant suspended in a high-concentration acrylamide solution was put in an incubator to completely deactivate the comparative strain through heat treatment conducted at 50° C. for 30 minutes. The remaining nitrile hydratase activity was measured as follows.

First, after the acrylamide treatment, the transformant was washed with a 50 mM phosphate buffer (pH 7.0) and the activity was measured by the following method. The washed transformant and 50 mM phosphate buffer (pH 7.0) were supplied to a test tube and preincubated at 30° C. for 10 minutes, and an equivalent volume of a 5% acrylonitrile solution (pH 7.0) was added and reacted for 10 minutes. Then, one tenth volume of 1 M phosphoric acid was added to terminate the reaction. Next, the transformant was removed from the terminated reaction mixture by a centrifuge, and the mixture was diluted to a proper concentration for analysis by HPLC (WAKOSIL 5C8 (Wako Pure Chemical Industries) 250 mm long, 10% acetonitrile containing 5 mM phosphoric acid, flow rate of mobile phase at 1 mL/min, wavelength of a UV absorption detector 260 nm). Using untreated cells for which acrylamide treatment was not conducted, activity was measured for comparison. Then, based on the obtained activity values, the activity remaining after the completion of acrylamide treatment was determined.

Among hundreds of transformants each containing a nitrile hydratase gene into which a mutation was introduced as above, four strains of mutant enzymes showing resistance to a high concentration of acrylamide were selected as shown in Table 3.

TABLE 3

| mutant strain No. | name of plasmid |
|---|---|
| 1 | pFR003 |
| 2 | pFR004 |
| 3 | pFR005 |
| 4 | pFR006 |

(4) Confirming Base Sequence

To confirm the base sequence of a nitrile hydratase gene, plasmid was recovered from the selected strains. The *Rhodococcus* transformant was inoculated into 10 mL of an MYK culture medium (0.5% polypeptone, 0.3% Bacto yeast extract, 0.3% malt extract, 1% glucose, 50 μg/mL kanamycin)

and incubated for 24 hours, and a 20% sterile glycine solution was added to make the final concentration of 2%, which was further incubated for another 24 hours. Then, the bacterial cells were recovered by a centrifuge, washed with TES buffer (10 mM Tris-HCl (pH8)-10 mM NaCl-1 mM EDTA), suspended in 2 mL of 50 mM Tris-HCl (pH8)-12.5% sucrose-100 mM NaCl-1 mg/mL lysozyme, and shaken at 37° C. for 3 hours. Then, 0.4 mL of 10% SDS was added and the mixture was shaken gently for an hour at room temperature, to which 2.1 mL of 5 M sodium acetate buffer (pH 5.2) was added and let stand in ice for an hour. Next, the mixture was centrifuged for an hour at 10,000×g at 4° C. to obtain a supernatant, to which a 5-times volume of ethanol was added and let stand at −20° C. for 30 minutes. Then, the mixture was centrifuged at 10,000×g for 20 minutes. The precipitant was washed with 10 mL of 70% ethanol and dissolved in 100 μL of a TE buffer. Accordingly, a DNA solution was obtained.

Next, the sequence including a nitrile hydratase was amplified by a PCR method.

<Composition of PCR Reaction Mixture>

| template plasmid | 1 μL |
| 10× PCR buffer (made by NEB) | 10 μL |
| primer NH-19 (50 μM) | 1 μL |
| primer NH-20 (50 μM) | 1 μL |
| 2.5 mM dNTPmix | 8 μL |
| sterile water | 79 μL |
| Taq DNA polymerase (made by NEB) | 1 μL |

<Primers>

```
                                        (SEQ ID NO: 7)
NH-19: GCCTCTAGATATCGCCATTCCGTTGCCGG (SEQ ID NO: 8)
NH-20: ACCCTGCAGGCTCGGCGCACCGGATGCCCAC
```

<Reaction Conditions>
(94° C. for 30 sec, 65° C. for 30 sec, 72° C. for 3 min)×30 cycles After completion of PCR, 5 μL of the reaction mixture was subjected to 0.7% agarose gel electrophoresis to detect a PCR amplified fragment of 2.5 kb. After Exo-SAP treatment (Amersham Pharmacia Biotech) on the PCR reaction mixture, samples for alignment analysis were prepared by a cycle sequencing method, and were analyzed using CEQ-2000XL (Beckman Coulter, Inc). The results are shown in Table 4.

TABLE 4

| name of plasmid | mutation site |
|---|---|
| pSJ 034 | no mutation site |
| pER 855A (template) | Nβ167S, Vβ219A, Sβ57M, Kβ114Y, Tβ107K |
| pFR 003 | Nβ167S, Vβ219A, Sβ57M, Kβ114Y, Tβ107K, Pβ17D |
| pFR 004 | Nβ167S, Vβ219A, Sβ57M, Kβ114Y, Tβ107K, Pβ17H |
| pFR 005 | Nβ167S, Vβ219A, Sβ57M, Kβ114Y, Tβ107K, Pβ17G |
| pFR 006 | Nβ167S, Vβ219A, Sβ57M, Kβ114Y, Tβ107K, Pβ17S |

(5) Evaluation of Amide-Compound Resistance

The amide-compound resistance of the improved nitrile hydratases obtained in (4) above was evaluated by the following method.

ATCC12674/pER855A and each transformant obtained in step (2) above were brought into contact with 10 mL of an MYK culture medium (50 μg/mL kanamycin), and subjected to shaking culture at 30° C. for 2 days. Then, 1% of each culture was inoculated into 100 mL of a GGPK culture medium (1.5% glucose, 1% sodium glutamate, 0.1% yeast extract, 0.05% $K_2HPO_4$, 0.05% $KH_2PO_4$, 0.05% $MgSO_4.7H_2O$, 1% $CoCl_2$, 0.1% urea, 50 μg/mL kanamycin, pH 7.2), and subjected to shaking culture at 30° C. for 3 days. Then, bacterial cells were collected by centrifugation.

The enzyme activity of the obtained cultured cells was measured by the following method: 0.2 mL of the bacterial cell mixture and 4.8 mL of a 50 mM phosphate buffer (pH 7.0) were mixed, to which 5 mL of a 50 mM phosphate buffer (pH 7.0) containing 5.0% (w/v) acrylonitrile was further added. Next, the mixture was reacted while being shaken at 10° C. for 10 minutes. Then, bacterial cells were filtered and the amount of produced acrylamide was measured using gas chromatography.

<Analysis Conditions>
analysis instrument: gas chromatograph GC-14B (Shimadzu Corporation)
detector: FID (detection at 200° C.)
column: 1 m glass column filled with PoraPak PS (column filler made by Waters Corp.)
column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U.

Next, experiments were conducted by setting the composition of a reaction mixture and reaction conditions below. Using the enzyme activity measured in advance, each bacterial suspension used for reaction was properly diluted by 100 mM phosphate buffer (pH 7.0) so that the amount of activity is set to be the same. ATCC 12674/pER855A was used as a comparison strain.

<Composition of Reaction Mixture>

| 50% acrylamide solution: | 94 g |
| acrylonitrile | 4 g |
| 1M phosphate buffer: | 1 g | bacterial fluid (same unit (U) of enzymatic activity)
<Reaction Conditions>
reaction for 5 hours while being stirred (30° C.)

Before the start of reaction (0 hour) and 5 hours after the start of reaction, 1 mL of the reaction mixture was taken for sampling, which was then filtered by a 0.45 μm filter. The obtained filtrate was put through gas chromatography. The proportion of remaining acrylonitrile was analyzed. The results are shown in Table 5.

TABLE 5

| | proportion of acrylonitrile (%) | | consumption | consumption |
|---|---|---|---|---|
| name of plasmid | before reaction starts (A) | 5 hrs after reaction starts (B) | amount of acrylonitrile (A − B) | rate of acrylonitrile (%) |
| pER 855A (comparative example) | 4.01 | 0.81 | 3.20 | 100 |
| pFR 003 | 4.01 | 0.70 | 3.31 | 103 |
| pFR 004 | 4.01 | 0.36 | 3.65 | 114 |
| pFR 005 | 4.01 | 0.40 | 3.61 | 113 |
| pFR 006 | 4.01 | 0.66 | 3.35 | 105 |

From the results above, in all the improved nitrile hydratases, the consumption rates of acrylonitrile exceeded 103% relative to the result of comparative example pER855A set at 100%. Thus, it is found that nitrile hydratase activity was maintained in the presence of high-concentration acrylamide and that resistance to acrylamide is enhanced in improved nitrile hydratase.

Example 2

Obtaining Improved Nitrile Hydratase Gene and Evaluation Thereof (2)
(1) Introduction of Mutation into Nitrile Hydratase and Selection Thereof Using pFR005 obtained in Example 1 as a template, an attempt was made to obtain an improved nitrile hydratase having further enhanced acrylamide resistance. The same procedures were employed as in Example 1 (introducing mutation, forming *Rhodococcus* transformant, amide processing of *Rhodococcus* transformant, confirming base sequence) except that the primers were changed, and mutant enzymes shown in Table 6 were obtained.

<Primers>
primer for saturation mutagenesis at β15

(SEQ ID NO: 9)
β15RM-F: atgaccggatacggaNNSgtccccctatcagaag (SEQ ID NO: 10)
β15RM-R: cttctgatagggggacSNNtccgtatccggtcat primer for saturation mutagenesis at β95

(SEQ ID NO: 11)
β95RM-F: accgaagaagagcgaNNScaccgtgtgcaagag (SEQ ID NO: 12)
β95RM-R: ctcttgcacacggtgSNNtcgctcttcttcggt primer for saturation mutagenesis at β105

(SEQ ID NO: 13)
β105RM-F: GAGATCCTTGAGGGTNNSTACACGGACAGG (SEQ ID NO: 14)
β105RM-R: CCTGTCCGTGTASNNACCCTCAAGGATCTC primer for saturation mutagenesis at β133

(SEQ ID NO: 15)
β133RM-F: cacgagccccactccNNSgcgcttccaggagcg (SEQ ID NO: 16)
β133RM-R: cgctcctggaagcgcSNNggagtggggctcgtg saturation mutagenesis primer at β144

(SEQ ID NO: 17)
β144RM-F: ggagccgagtttctctNNSggtgacaagatc (SEQ ID NO: 18)
β144RM-R: gatcttgtcaccSNNagagaaactcggctcc primer for saturation mutagenesis at β168

(SEQ ID NO: 19)
β168RM-F: cgaaatatgtgcggagcNNSatcggggaaatcg (SEQ ID NO: 20)
β168RM-R: cgatttccccgatSNNgctccgcacatatttcg primer for saturation mutagenesis at β190

(SEQ ID NO: 21)
β190RM-F: gagcagctccgccggcctcNNSgacgatcctcg (SEQ ID NO: 22)
β190RM-R: cgaggatcgtcSNNgaggccggcggagctgctc primer for saturation mutagenesis at α124

(SEQ ID NO: 23)
α124RM-F: gtacaagagcatgNNStaccggtcccgagtgg (SEQ ID NO: 24)
α124RM-R: ccactcgggaccggtaSNNcatgctcttgtac

TABLE 6

| name of plasmid | mutation site |
| --- | --- |
| pFR005 (template) | Nβ167S, Vβ219A, Sβ57M, Kβ114Y, Tβ107K, Pβ17G |
| pFR102 | Nβ167S, Vβ219A, Sβ57M, Kβ114Y, Tβ107K, Pβ17S, Rβ105W |
| pFR108A | Nβ167S, Vβ219A, Sβ57M, Kβ114Y, Tβ107K, Pβ17S, Lβ144S |
| pFR109 | Nβ167S, Vβ219A, Sβ57M, Kβ114Y, Tβ107K, Pβ17S, Kβ168R |
| pFR112 | Nβ167S, Vβ219A, Sβ57M, Kβ114Y, Tβ107K, Pβ17S, Eα↓17S |
| pFR116 | Nβ167S, Vβ219A, Sβ57M, Kβ114Y, Tβ107K, Pβ17S, Gβ190H |
| pFR119 | Nβ167S, Vβ219A, Sβ57M, Kβ114Y, Tβ107K, Pβ17S, Kβ95V |
| pFR120 | Nβ167S, Vβ219A, Sβ57M, Kβ114Y, Tβ107K, Pβ17S, Lβ133N |
| pFR121 | Nβ167S, Vβ219A, Sβ57M, Kβ114Y, Tβ107K, Pβ17S, Lβ133R |
| pFR122 | Nβ167S, Vβ219A, Sβ57M, Kβ114Y, Tβ107K, Pβ17S, Pβ15S |

(2) Performance Evaluation

The performance of obtained improved nitrile hydratases was evaluated by the same method as in (5) of Example 1.

TABLE 7

| | proportion of acrylonitrile (%) | | consumption | |
| --- | --- | --- | --- | --- |
| name of plasmid | before reaction starts (A) | 5 hrs after reaction starts (B) | amount of acrylonitrile (A − B) | consumption rate of acrylonitrile |
| pER855A (comp example) | 4.01 | 0.81 | 3.20 | 100 |
| pFR102 | 4.01 | 0.15 | 3.86 | 121 |
| pFR108A | 4.01 | 0.15 | 3.86 | 121 |
| pFR109 | 4.01 | 0.25 | 3.76 | 118 |
| pFR112 | 4.01 | 0.17 | 3.84 | 120 |
| pFR116 | 4.01 | 0.15 | 3.86 | 121 |
| pFR119 | 4.01 | 0.25 | 3.76 | 117 |
| pFR120 | 4.01 | 0.15 | 3.86 | 121 |
| pFR121 | 4.01 | 0.05 | 3.96 | 124 |
| pFR122 | 4.01 | 0.21 | 3.80 | 119 |

From the results above, in all the improved nitrile hydratases, the consumption rates of acrylonitrile exceeded 117% relative to the result of comparative example pER855A set at 100%. Thus, it is found that nitrile hydratase activity was maintained in the presence of high-concentration acrylamide and that resistance to acrylamide is enhanced in improved nitrile hydratase.

Example 3

Obtaining Improved Nitrile Hydratase Gene and Evaluation Thereof (3)

(1) Introduction of Mutation into Nitrile Hydratase and Selection Thereof

Using pFR108A obtained in Example 2 as a template, an attempt was made to obtain an improved nitrile hydratase having further enhanced acrylamide resistance. The same procedures were employed as in Example 1 (introducing mutation, forming *Rhodococcus* transformant, amide processing of *Rhodococcus* transformant, confirming base sequence) except that the primers were changed, and mutant enzymes shown in Table 8 were obtained. Selection of transformant containing an improved nitrile hydratase was conducted using the same method as in Example 1 except that heat treatment was conducted at 55° C. for 60 minutes.

<Primers>
primer for saturation mutagenesis at α174

```
                                          (SEQ ID NO: 25)
α174RM-F: gccggcaccgacNNStggtccgaggag (SEQ ID NO: 26)
α174RM-R: ctcctcggaccaSNNgtcggtgccggc
```

TABLE 8

| name of plasmid | mutation site |
| --- | --- |
| pFR108A (template) | Nβ167S, Vβ219A, Sβ57M, Kβ114Y, Tβ107K, Pβ17S, Lβ144S |
| pFR211 | Nβ167S, Vβ219A, Sβ57M, Kβ114Y, Tβ107K, Pβ17S, Lβ144S, Gα↓67L |
| pFR212 | Nβ167S, Vβ219A, Sβ57M, Kβ114Y, Tβ107K, Pβ17S, Lβ144S, Gα↓67V |

(2) Performance Evaluation

The performance of obtained improved nitrile hydratase was evaluated by the same method as in (5) of Example 1.

TABLE 9

| | proportion of acrylonitrile (%) | | consumption | |
| --- | --- | --- | --- | --- |
| name of plasmid | before reaction starts (A) | 5 hrs after reaction starts (B) | amount of acrylonitrile (A − B) | consumption rate of acrylonitrile |
| pER855A (comp example) | 4.01 | 0.81 | 3.20 | 1.00 |
| pFR211 | 4.01 | 0.05 | 3.96 | 1.24 |
| pFR212 | 4.01 | 0.05 | 3.96 | 1.24 |

From the results above, in all the improved nitrile hydratases, the consumption rates of acrylonitrile exceeded 124% relative to the result of comparative example pER855A set at 100%. Thus, it is found that nitrile hydratase activity was maintained in the presence of high-concentration acrylamide and that resistance to acrylamide is enhanced in improved nitrile hydratase.

Example 4

(1) Introduction of Mutation into Nitrile Hydratase and Selection Thereof

Using pFR211 obtained in Example 2 as a template, an attempt was made to obtain an improved nitrile hydratase having further enhanced acrylamide resistance. The same procedures were used as in Example 3 (introducing mutation, forming *Rhodococcus* transformant, amide processing of *Rhodococcus* transformant, confirming base sequence) except that the primers were changed, and mutant enzymes shown in Table 10 were obtained.

<Primers>
primer for saturation mutagenesis at β95

```
                                          (SEQ ID NO: 27)
β95RM-F: accgaagaagagcgaNNScaccgtgtgcaagag (SEQ ID NO: 28)
β95RM-R: ctcttgcacacggtgSNNtcgctcttcttcggt
``` primer for saturation mutagenesis at β112

```
                                          (SEQ ID NO: 29)
β112RM-F: GACAGGAAGCCGNNSCGGAAGTTCGATCCG (SEQ ID NO: 30)
β112RM-R: CGGATCGAACTTCCGSNNCGGCTTCCTGTC
``` primer for saturation mutagenesis at β218

```
                                          (SEQ ID NO: 31)
β218RM-F: gggaaagacgtagtgNNSgccgatctctgggaa (SEQ ID NO: 32)
β218RM-R: ttcccagagatcggcSNNcactacgtctttccc
```

TABLE 10

| name of plasmid | mutation site |
| --- | --- |
| pFR303 | Nβ167S, Vβ219A, Sβ57M, Kβ114Y, Tβ107K, Pβ17S, Lβ144S, Gα↓67L, Kβ95V |
| pFR304 | Nβ167S, Vβ219A, Sβ57M, Kβ114Y, Tβ107K, Pβ17S, Lβ144S, Gα↓67L, Sβ112T |
| pFR306 | Nβ167S, Vβ219A, Sβ57M, Kβ114Y, Tβ107K, Pβ17S, Lβ144S, Gα↓67L, Cβ218H |

(2) Performance Evaluation

The performance of obtained improved nitrile hydratases was evaluated by the same method as in (5) of Example 1. The results are shown in Table 11

TABLE 11

| | proportion of acrylonitrile (%) | | consumption | |
| --- | --- | --- | --- | --- |
| name of plasmid | before reaction starts (A) | 3 hrs after reaction starts (B) | amount of acrylonitrile (A − B) | consumption rate of acrylonitrile |
| pER855A (comp example) | 4.01 | 0.81 | 3.20 | 1.00 |
| pFR303 | 4.01 | 0.00 | 4.01 | 1.25 |
| pFR304 | 4.01 | 0.00 | 4.01 | 1.25 |
| pFR306 | 4.01 | 0.00 | 4.01 | 1.25 |

From the results above, in all the improved nitrile hydratases, the consumption rates of acrylonitrile exceeded 125% relative to the result of comparative example pER855A set at 100%. Thus, it is found that nitrite hydratase activity was maintained in the presence of high-concentration acrylamide and that resistance to acrylamide is enhanced in improved nitrile hydratase.

Example 5

(1) Producing pFR306A

Using pFR306 obtained in Example 4 as a template, an improved nitrile hydratase was produced by substituting Lβ144S with a wild-type amino acid. A *Rhodococcus* transformant was produced using the same method as in Example 1 and the primers below.
<Primers>
mutation at β144 is returned to a wild type

```
                                    (SEQ ID NO: 33)
F-Sβ144L-F: TTCTCTCTCGGTGACAAGATCAAAGTG (SEQ ID NO: 34)
F-Sβ144L-R: GTCACCGAGAGAGAAACTCGGCTCCGC
```

TABLE 12

| name of plasmid | mutation site |
| --- | --- |
| pFR306A | Nβ167S, Vβ219A, Sβ57M, Kβ114Y, Tβ107K, Pβ17S, Gα↓67L, Cβ218H |

(2) Evaluation of Heat Resistivity

Performance of improved nitrile hydratases obtained in the present invention was evaluated as follows.

Transformants containing mutant nitrile hydratase genes shown in Table 13 were incubated by the method in (5) of Example 1 to evaluate heat resistivity. After the cultures were diluted properly by a 50 mM phosphate buffer and heated in a 70° C. water bath for 10 minutes, remaining nitrile hydratase activity was determined by the method described in (5) of Example 1. For comparison, untreated bacteria samples were prepared by not heating the cultures but keeping them at 4° C., and their respective remaining activity was determined.

TABLE 13

| name of plasmid | mutation site |
| --- | --- |
| pER855A (comp example) | Nβ167S, Vβ219A, Sβ57M, Kβ114Y, Tβ107K |
| pFR005 | Nβ167S, Vβ219A, Sβ57M, Kβ114Y, Tβ107K, Pβ17S |
| pFR108A | Nβ167S, Vβ219A, Sβ57M, Kβ114Y, Tβ107K, Pβ17S, Lβ144S |
| pFR211 | Nβ167S, Vβ219A, Sβ57M, Kβ114Y, Tβ107K, Pβ17S, Lβ144S, Gα↓67L |
| pFR303 | Nβ167S, Vβ219A, Sβ57M, Kβ114Y, Tβ107K, Pβ17S, Lβ144S, Gα↓67L, Kβ95V |
| pFR304 | Nβ167S, Vβ219A, Sβ57M, Kβ114Y, Tβ107K, Pβ17S, Lβ144S, Gα↓67L, Sβ112T |
| pFR306 | Nβ167S, Vβ219A, Sβ57M, Kβ114Y, Tβ107K, Pβ17S, Lβ144S, Gα↓67L, Cβ218H |
| pFR306A | Nβ167S, Vβ219A, Sβ57M, Kβ114Y, Tβ107K, Pβ17S, Gα↓67L, Cβ218H |

When the remaining activity of comparative example pER855A was set as 1 (11%), the remaining activity of each of all the improved nitrile hydratases was at least 3 times (30%) as great. Thus, the heat resistivity of improved nitrile hydratases was found to be enhanced.

Example 6

Using transformants obtained in Example 5, their acrylamide accumulation properties during high-temperature reactions was evaluated.

In a plastic tube with a lid, 10 mL of a 50 mM phosphate buffer and a transformant were added and preincubated for 10 minutes while the tube was shaken in a 40° C. water bath. Next, 1 mL of acrylonitrile was added to each reaction mixture and a reaction was started. After the start of the reaction, 1 mL each of acrylonitrile at predetermined timing (20 minutes, 40 minutes, 1 hour, 1½ hours, 2 hours) was added to continue the reaction. The reaction mixture 3 hours after the start of the reaction was filtered and the acrylamide concentration of the filtrate was determined by gas chromatography.

As a result of the experiment, 32% of the acrylamide was accumulated in comparative example pER855A while over 40% of the acrylamide was accumulated in each improved nitrile hydratase. Accordingly, improved nitrile hydratases were found to have enhanced high-temperature accumulation properties.

INDUSTRIAL APPLICABILITY

An improved nitrile hydratase is provided by the present invention. In the improved nitrile hydratase of the present invention, heat resistance, amide-compound resistance and high-temperature accumulation properties are enhanced. Thus, using the improved nitrile hydratase of the present invention, amide compounds are produced efficiently from nitrite compounds.

[Details of Sequence Listing]
SEQ ID NO:1 base sequence in β subunit of a nitrile hydratase derived from J1 strain
SEQ ID NO:2 amino-acid sequence in β subunit of a nitrile hydratase derived from J1 strain
SEQ ID NO:3 base sequence in α subunit of a nitrile hydratase derived from J1 strain
SEQ ID NO:4 amino-acid sequence in α subunit of a nitrile hydratase derived from J1 strain
SEQ ID NO:5 primer for saturation mutagenesis at β17
SEQ ID NO:6 primer for saturation mutagenesis at β17
SEQ ID NO:7 NH-19 primer
SEQ ID NO:8 NH-20 primer
SEQ ID NO:9 primer for saturation mutagenesis at β15
SEQ ID NO:10 primer for saturation mutagenesis at β15
SEQ ID NO:11 primer for saturation mutagenesis at β95
SEQ ID NO:12 primer for saturation mutagenesis at β95
SEQ ID NO:13 primer for saturation mutagenesis at β105
SEQ ID NO:14 primer for saturation mutagenesis at β105
SEQ ID NO:15 primer for saturation mutagenesis at β133
SEQ ID NO:16 primer for saturation mutagenesis at β133
SEQ ID NO:17 primer for saturation mutagenesis at β144
SEQ ID NO:18 primer for saturation mutagenesis at β144
SEQ ID NO:19 primer for saturation mutagenesis at β168
SEQ ID NO:20 primer for saturation mutagenesis at β168
SEQ ID NO:21 primer for saturation mutagenesis at β190
SEQ ID NO:22 primer for saturation mutagenesis at β190
SEQ ID NO:23 primer for saturation mutagenesis at α124
SEQ ID NO:24 primer for saturation mutagenesis at α124
SEQ ID NO:25 primer for saturation mutagenesis at α174
SEQ ID NO:26 primer for saturation mutagenesis at α174
SEQ ID NO:27 primer for saturation mutagenesis at β95

SEQ ID NO:28 primer for saturation mutagenesis at β95
SEQ ID NO:29 primer for saturation mutagenesis at β112
SEQ ID NO:30 primer for saturation mutagenesis at β112
SEQ ID NO:31 primer for saturation mutagenesis at β218
SEQ ID NO:32 primer for saturation mutagenesis at β218
SEQ ID NO:33 primer to return mutation at β144 to a wild type
SEQ ID NO:34 primer to return mutation at β144 to a wild type
SEQ ID NO:35 β subunit of *Rhodococcus* M8
SEQ ID NO:36 β subunit of *Rhodococcus ruber* TH
SEQ ID NO:37 β subunit of *R. pyridinovorans* MW3
SEQ ID NO:38 β subunit of *R. pyridinovorans* S85-2
SEQ ID NO:39 β subunit of *R. pyridinovorans* MS-38
SEQ ID NO:40 β subunit of *Nocardia* sp. JBRs
SEQ ID NO:41 β subunit of *Nocardia* sp. YS-2002
SEQ ID NO:42 β subunit of *R. rhodocrous* ATCC39384
SEQ ID NO:43 β subunit of uncultured bacterium SP1
SEQ ID NO:44 β subunit of uncultured bacterium BD2
SEQ ID NO:45 β subunit of *Comamonas testosteroni*
SEQ ID NO:46 β subunit of *G. thermoglucosidasius* Q6
SEQ ID NO:47 β subunit of *P. thermophila* JCM 3095
SEQ ID NO:48 β subunit of *R. rhodocrous* Cr4
SEQ ID NO:49 α subunit of *Rhodococcus* M8
SEQ ID NO:50 α subunit of *Rhodococcus ruber* TH
SEQ ID NO:51 α subunit of *R. pyridinovorans* MW3
SEQ ID NO:52 α subunit of *R. pyridinovorans* S85-2
SEQ ID NO:53 α subunit of *Nocardia* sp. JBRs
SEQ ID NO:54 α subunit of *Nocardia* sp. YS-2002
SEQ ID NO:55 α subunit of uncultured bacterium BD2
SEQ ID NO:56 α subunit of uncultured bacterium SP1
SEQ ID NO:57 α subunit of *R. rhodocrous* ATCC39484
SEQ ID NO:58 α subunit of *Sinorhizobium medicae* WSM419
SEQ ID NO:59 α subunit of *P. thermophila* JCM 3095
SEQ ID NO:60 α subunit of *R. rhodocrous* Cr4
SEQ ID NO:61 cysteine cluster in α subunit of iron-containing nitrile hydratase derived from *Rhodococcus* N-771 strain
SEQ ID NO:62 cysteine cluster in α subunit of cobalt-containing nitrile hydratase derived from J1 strain

What is claimed is:

1. An isolated cDNA encoding a nitrile hydratase protein having higher heat resistance and acylamide resistance than heat resistance and acylamide resistance of the wild type nitrile hydratase protein comprising (1) a β subunit amino acid sequence having at least 90% homology to the β subunit amino acid sequence set forth in SEQ ID NO: 2 wherein amino-acid residues corresponding to amino acid residues at positions 57, 107, 114, 167 and 219 in the amino-acid sequence of SEQ ID NO: 2 are substituted with amino-acid residues that are different than the amino acid residues at the corresponding positions in SEQ ID NO: 2, and (2) an α subunit amino acid sequence having at least 90% homology to the α subunit amino acid sequence of SEQ ID NO: 4, and (3) wherein said encoded nitrile hydratase protein comprises one or more further amino acid substitutions in either or both of said α and β subunit amino acid sequences at:

(i) amino acid residues at positions corresponding to positions 15, 17, 95, 105, 112, 133, 144, 168, 190 or 218 of SEQ ID NO: 2 with amino acid residues that are different than the amino acid residues at the corresponding positions in SEQ ID NO: 2, and (ii) amino acid residues at positions corresponding to positions 124 and 171 in the amino-acid sequence of the a subunit of SEQ ID NO: 4 that are different than the amino acid residues at the corresponding positions in SEQ ID NO: 4.

2. The cDNA according to claim 1, wherein the residues corresponding to amino-acid residues at the positions 57, 107, 114, 167 and 219 in the amino-acid sequence of the β subunit of SEQ ID NO: 2 are substituted by Methionine (M), Lysine (K), Tyrosine (Y), Serine (S), and Alanine (A), respectively.

3. The cDNA according to claim 1, wherein the amino acid residue corresponding to the position 15 in the β submit amino-acid sequence of SEQ ID NO: 4 is substituted by Serine (S);

the amino acid residue corresponding to the position 17 in the β submit amino-acid sequence of SEQ ID NO: 4 is substituted by Aspartic acid (D), Histidine (H), Glycine (G) or Serine (S);

the amino acid residue corresponding to the position 95 in the β submit amino-acid sequence of SEQ ID NO: 4 is substituted by Valine (V);

the amino acid residue corresponding to the position 105 in the β submit amino-acid sequence of SEQ ID NO: 4 is substituted by Tryptophan (W);

the amino acid residue corresponding to the position 112 in the β submit amino-acid sequence of SEQ ID NO: 4 is substituted by Threonine (T);

the amino acid residue corresponding to the position 133 in the β submit amino-acid sequence of SEQ ID NO: 4 is substituted by Asparagine (N) or Arginine (R);

the amino acid residue corresponding to the position 144 in the β submit amino-acid sequence of SEQ ID NO: 4 is substituted by Arginine (R) or Serine (S);

the amino acid residue corresponding to the position 168 in the β submit amino-acid sequence of SEQ ID NO: 4 is substituted by Arginine (R);

the amino acid residue corresponding to the position 190 in the β submit amino-acid sequence of SEQ ID NO: 4 is substituted by Histidine (H);

the amino acid residue corresponding to the position 218 in the β submit amino-acid sequence of SEQ ID NO: 4 is substituted by Histidine (H);

the amino acid residue corresponding to the position 124 of the β subunit of SEQ ID NO: 4 is substituted by Serine (S);

the amino acid residue corresponding to the position 174 of the α subunit of SEQ ID NO: 4 is substituted by Leucine (L) or Valine (V); or any combination thereof.

4. The cDNA according to claim 2, wherein the amino acid residue corresponding to the position 15 in the β submit amino-acid sequence of SEQ ID NO: 4 is substituted by Serine (S);

the amino acid residue corresponding to the position 17 in the β submit amino-acid sequence of SEQ ID NO: 4 is substituted by Aspartic acid (D), Histidine (H), Glycine (G) or Serine (S);

the amino acid residue corresponding to the position 95 in the β submit amino-acid sequence of SEQ ID NO: 4 is substituted by Valine (V);

the amino acid residue corresponding to the position 105 in the β submit amino-acid sequence of SEQ ID NO: 4 is substituted by Tryptophan (W);

the amino acid residue corresponding to the position 112 in the β submit amino-acid sequence of SEQ ID NO: 4 is substituted by Threonine (T);

the amino acid residue corresponding to the position 133 in the β submit amino-acid sequence of SEQ ID NO: 4 is substituted by Asparagine (N) or Arginine (R);

the amino acid residue corresponding to the position 144 in the β submit amino-acid sequence of SEQ ID NO: 4 is substituted by Arginine (R) or Serine (S);

the amino acid residue corresponding to the position 168 in the β submit amino-acid sequence of SEQ ID NO: 4 is substituted by Arginine (R);

the amino acid residue corresponding to the position 190 in the β submit amino-acid sequence of SEQ ID NO: 4 is substituted by Histidine (H);

the amino acid residue corresponding to the position 218 in the β submit amino-acid sequence of SEQ ID NO: 4 is substituted by Histidine (H);

the amino acid residue corresponding to the position 124 of the α subunit of SEQ ID NO: 4 is substituted by Serine (S);

the amino acid residue corresponding to the position 174 of the α subunit of SEQ ID NO: 4 is substituted by Leucine (L) or Valine (V); or any combination thereof.

5. A recombinant vector comprising the isolated cDNA according to claim 1.

6. A transformed cell comprising the recombinant vector according to claim 5.

7. A method for producing a nitrile hydratase comprising incubating the transformed cell according to claim 6 in a culture medium and collecting a nitrile hydratase from a culture of the transformed cell.

* * * * *

SEQUENCE LISTING

```
<160> NUMBER OF SEQ ID NOS: 62

<210> SEQ ID NO 1
<211> LENGTH: 690
<212> TYPE: DNA
<213> ORGANISM: Rhodococcus J1-H

<400> SEQUENCE: 1
atggatggta tccacgacac aggcggcatg accggatacg gaccggtccc ctatcagaag      60
gacgagccct tcttccacta cgagtgggag ggtcggaccc tgtcaattct gacttggatg     120
catctcaagg gcatatcgtg gtgggacaag tcgcggttct tccgggagtc gatggggaac     180
gaaaactacg tcaacgagat tcgcaactcg tactacaccc actggctgag tgcggcagaa     240
cgtatcctcg tcgccgacaa gatcatcacc gaagaagagc gaaagcaccg tgtgcaagag     300
atccttgagg gtcggtacac ggacaggaag ccgtcgcgga agttcgatcc ggcccagatc     360
gagaaggcga tcgaacggct tcacgagccc cactccctag cgcttccagg agcggagccg     420
agtttctctc tcggtgacaa gatcaaagtg aagagtatga acccgctggg acacacacgg     480
tgcccgaaat atgtgcggaa caagatcggg gaaatcgtcg cctaccacgg ctgccagatc     540
tatcccgaga gcagctccgc cggcctcggc gacgatcctc gcccgctcta cacggtcgcg     600
ttttccgccc aggaactgtg gggcgacgac ggaaacggga aagacgtagt gtgcgtcgat     660
ctctgggaac cgtacctgat ctctgcgtga                                       690

<210> SEQ ID NO 2
<211> LENGTH: 229
<212> TYPE: PRT
<213> ORGANISM: Rhodococcus J1-H

<400> SEQUENCE: 2

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
```

```
            50                  55                  60
Asn Glu Ile Arg Asn Ser Tyr Tyr Thr His Trp Leu Ser Ala Ala Glu
 65                  70                  75                  80

Arg Ile Leu Val Ala Asp Lys Ile Ile Thr Glu Glu Arg Lys His
                 85                  90                  95

Arg Val Gln Glu Ile Leu Glu Gly Arg Tyr Thr Asp Arg Lys Pro Ser
                100                 105                 110

Arg Lys Phe Asp Pro Ala Gln Ile Glu Lys Ala Ile Glu Arg Leu His
                115                 120                 125

Glu Pro His Ser Leu Ala Leu Pro Gly Ala Glu Pro Ser Phe Ser Leu
                130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Ile Val Ala Tyr His
                165                 170                 175

Gly Cys Gln Ile Tyr Pro Glu Ser Ser Ser Ala Gly Leu Gly Asp Asp
                180                 185                 190

Pro Arg Pro Leu Tyr Thr Val Ala Phe Ser Ala Gln Glu Leu Trp Gly
                195                 200                 205

Asp Asp Gly Asn Gly Lys Asp Val Val Cys Val Asp Leu Trp Glu Pro
                210                 215                 220

Tyr Leu Ile Ser Ala
225

<210> SEQ ID NO 3
<211> LENGTH: 612
<212> TYPE: DNA
<213> ORGANISM: Rhodococcus J1-H

<400> SEQUENCE: 3
gtgagcgagc acgtcaataa gtacacggag tacgaggcac gtaccaaggc gatcgaaacc        60
ttgctgtacg agcgagggct catcacgccc gccgcggtcg accgagtcgt ttcgtactac       120
gagaacgaga tcggcccgat gggcggtgcc aaggtcgtgg ccaagtcctg ggtggaccct       180
gagtaccgca agtggctcga agaggacgcg acggccgcga tggcgtcatt gggctatgcc       240
ggtgagcagg cacaccaaat ttcggcggtc ttcaacgact cccaaacgca tcacgtggtg       300
gtgtgcactc tgtgttcgtg ctatccgtgg ccggtgcttg gtctcccgcc cgcctggtac       360
aagagcatgg agtaccggtc ccgagtggta gcggaccctc gtggagtgct caagcgcgat       420
ttcggtttcg acatccccga tgaggtggag gtcaggggttt gggacagcag ctccgaaatc       480
cgctacatcg tcatcccgga acggccggcc ggcaccgacg gttggtccga ggaggagctg       540
acgaagctgg tgagccggga ctcgatgatc ggtgtcagta atgcgctcac accgcaggaa       600
gtgatcgtat ga                                                           612

<210> SEQ ID NO 4
<211> LENGTH: 203
<212> TYPE: PRT
<213> ORGANISM: Rhodococcus J1-H

<400> SEQUENCE: 4

Met Ser Glu His Val Asn Lys Tyr Thr Glu Tyr Glu Ala Arg Thr Lys
  1               5                  10                  15

Ala Ile Glu Thr Leu Leu Tyr Glu Arg Gly Leu Ile Thr Pro Ala Ala
                 20                  25                  30
```

Val Asp Arg Val Val Ser Tyr Tyr Glu Asn Glu Ile Gly Pro Met Gly
             35                  40                  45

Gly Ala Lys Val Val Ala Lys Ser Trp Val Asp Pro Glu Tyr Arg Lys
 50                  55                  60

Trp Leu Glu Glu Asp Ala Thr Ala Ala Met Ala Ser Leu Gly Tyr Ala
 65                  70                  75                  80

Gly Glu Gln Ala His Gln Ile Ser Ala Val Phe Asn Asp Ser Gln Thr
                 85                  90                  95

His His Val Val Val Cys Thr Leu Cys Ser Cys Tyr Pro Trp Pro Val
                100                 105                 110

Leu Gly Leu Pro Pro Ala Trp Tyr Lys Ser Met Glu Tyr Arg Ser Arg
            115                 120                 125

Val Val Ala Asp Pro Arg Gly Val Leu Lys Arg Asp Phe Gly Phe Asp
130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
            195                 200

<210> SEQ ID NO 5
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 5
ggatacggac cggtcnnsta tcagaaggac gag                           33

<210> SEQ ID NO 6
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 6
ctcgtccttc tgatasnnga ccggtccgta tcc                           33

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
gcctctagat atcgccattc cgttgccgg                               29

<210> SEQ ID NO 8

```
<211> LENGTH: 31
<212> TYPE: DNA
<213> ORGANISM: Artificial Sequence
<220> FEATURE:
<223> OTHER INFORMATION: Primer

<400> SEQUENCE: 8
accctgcagg ctcggcgcac cggatgccca c                              31

<210> SEQ ID NO 9
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 9
atgaccggat acggannsgt cccctatcag aag                            33

<210> SEQ ID NO 10
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 10
cttctgatag gggacsnntc cgtatccggt cat                            33

<210> SEQ ID NO 11
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 11
accgaagaag agcgannsca ccgtgtgcaa gag                            33

<210> SEQ ID NO 12
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 12
ctcttgcaca cggtgsnntc gctcttcttc ggt                            33

<210> SEQ ID NO 13
<211> LENGTH: 30
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 13
gagatccttg agggtnnsta cacggacagg                                   30

<210> SEQ ID NO 14
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is a, c, g, or t

<400> SEQUENCE: 14
cctgtccgtg tasnnaccct caaggatctc                                   30

<210> SEQ ID NO 15
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 15
cacgagcccc actccnnsgc gcttccagga gcg                               33

<210> SEQ ID NO 16
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 16
cgctcctgga agcgcsnngg agtggggctc gtg                               33

<210> SEQ ID NO 17
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 17
ggagccgagt ttctctnnsg gtgacaagat c                                 31

<210> SEQ ID NO 18
<211> LENGTH: 31
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is a, c, g, or t

<400> SEQUENCE: 18
gatcttgtca ccsnnagaga aactcggctc c                                    31

<210> SEQ ID NO 19
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(19)
<223> OTHER INFORMATION: n is a, c, g, or t

<400> SEQUENCE: 19
cgaaatatgt gcggagcnns atcggggaaa tcg                                  33

<210> SEQ ID NO 20
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(16)
<223> OTHER INFORMATION: n is a, c, g, or t

<400> SEQUENCE: 20
cgatttcccc gatsnngctc cgcacatatt tcg                                  33

<210> SEQ ID NO 21
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(21)
<223> OTHER INFORMATION: n is a, c, g, or t

<400> SEQUENCE: 21
gagcagctcc gccggcctcn nsgacgatcc tcg                                  33

<210> SEQ ID NO 22
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 22
cgaggatcgt csnngaggcc ggcggagctg ctc                                  33

<210> SEQ ID NO 23
<211> LENGTH: 32
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is a, c, g, or t

<400> SEQUENCE: 23
gtacaagagc atgnnstacc ggtcccgagt gg                                  32

<210> SEQ ID NO 24
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(19)
<223> OTHER INFORMATION: n is a, c, g, or t

<400> SEQUENCE: 24
ccactcggga ccggtasnnc atgctcttgt ac                                  32

<210> SEQ ID NO 25
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 25
gccggcaccg acnnstggtc cgaggag                                        27

<210> SEQ ID NO 26
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is a, c, g, or t

<400> SEQUENCE: 26
ctcctcggac casnngtcgg tgccggc                                        27

<210> SEQ ID NO 27
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 27
accgaagaag agcgannsca ccgtgtgcaa gag                                 33

<210> SEQ ID NO 28
```

```
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 28
ctcttgcaca cggtgsnntc gctcttcttc ggt                              33

<210> SEQ ID NO 29
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 29
gacaggaagc cgnnscggaa gttcgatccg                                  30

<210> SEQ ID NO 30
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 30
cggatcgaac ttccgsnncg gcttcctgtc                                  30

<210> SEQ ID NO 31
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 31
gggaaagacg tagtgnnsgc gatctctggg aa                               32

<210> SEQ ID NO 32
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t

<400> SEQUENCE: 32
ttcccagaga tcggcsnnca ctacgtcttt ccc                              33
```

```
<210> SEQ ID NO 33
<211> LENGTH: 27
<212> TYPE: DNA
<213> ORGANISM: Artificial Sequence
<220> FEATURE:
<223> OTHER INFORMATION: Primer

<400> SEQUENCE: 33
ttctctctcg gtgacaagat caaagtg                                              27

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
gtcaccgaga gagaaactcg gctccgc                                              27

<210> SEQ ID NO 35
<211> LENGTH: 229
<212> TYPE: PRT
<213> ORGANISM: Rhodococcus M8

<400> SEQUENCE: 35

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225

<210> SEQ ID NO 36
<211> LENGTH: 229
```

```
<212> TYPE: PRT
<213> ORGANISM: Rhodococcus ruber TH

<400> SEQUENCE: 36

Met Asp Gly Ile His Asp Thr Gly Gly Met Thr Gly Tyr Gly Pro Val
1               5                   10                  15

Pro Tyr Gln Lys Asp Glu Pro Phe His Tyr Glu Trp Glu Gly Arg
            20                  25                  30

Thr Leu Ser Ile Leu Thr Trp Met His Leu Lys Gly Met Ser Trp Trp
                35                  40                  45

Asp Lys Ser Arg Phe Phe Arg Glu Ser Met Gly Asn Glu Asn Tyr Val
            50                  55                  60

Asn Glu Ile Arg Asn Ser Tyr Tyr Thr His Trp Leu Ser Ala Ala Glu
65              70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Ser Lys Ile Gly Glu Ile Val Thr Ser His
                165                 170                 175

Gly Cys Gln Ile Tyr Pro Glu Ser Ser Ala Gly Leu Gly Asp Asp
            180                 185                 190

Pro Arg Pro Leu Tyr Thr Val Ala Phe Ser Ala Gln Leu Trp Gly
            195                 200                 205

Asp Asp Gly Asn Gly Lys Asp Val Val Cys Ala Asp Leu Trp Glu Pro
        210                 215                 220

Tyr Leu Ile Ser Ala
225

<210> SEQ ID NO 37
<211> LENGTH: 229
<212> TYPE: PRT
<213> ORGANISM: Rhodococcus pyridinovorans MW3

<400> SEQUENCE: 37

Met Asp Gly Ile His Gly Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
                35                  40                  45

Asp Lys Ser Arg Phe Phe Arg Glu Ser Met Gly Asn Glu Asn Tyr Val
            50                  55                  60

Asn Glu Ile Arg Asn Ser Tyr Tyr Thr His Trp Leu Ser Ala Ala Glu
65              70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
            100                 105                 110
```

```
Arg Lys Phe Asp Pro Ala Gln Ile Glu Lys Ala Ile Glu Arg Leu His
            115                 120                 125
Glu Pro His Ser Leu Ala Leu Pro Gly Ala Glu Pro Ser Phe Ser Leu
        130                 135                 140
Gly Asp Lys Ile Lys Val Lys Ser Met Asn Pro Leu Glu His Thr Arg
145                 150                 155                 160
Cys Pro Lys Tyr Val Arg Asn Lys Ile Gly Glu Ile Val Thr Tyr His
                165                 170                 175
Gly Cys Gln Ile Tyr Pro Glu Ser Ser Ala Gly Leu Gly Asp Asp
            180                 185                 190
Pro Arg Pro Leu Tyr Thr Val Ala Phe Ser Ala Gln Glu Leu Trp Gly
        195                 200                 205
Asp Asp Gly Asn Gly Lys Asp Val Val Cys Val Asp Leu Trp Glu Pro
    210                 215                 220
Tyr Leu Ile Ser Ala
225

<210> SEQ ID NO 38
<211> LENGTH: 229
<212> TYPE: PRT
<213> ORGANISM: Rhodococcus pyridinovorans S85-2

<400> SEQUENCE: 38

Met Asp Gly Ile His Gly Thr Gly Gly Met Thr Gly Tyr Gly Pro Val
1               5                   10                  15
Pro Tyr Gln Lys Asp Glu Pro Phe Phe His Tyr Glu Trp Glu Gly Arg
            20                  25                  30
Thr Leu Ser Ile Leu Thr Trp Met His Leu Lys Gly Ile Ser Trp Trp
        35                  40                  45
Asp Lys Ser Arg Phe Phe Arg Glu Ser Met Gly Asn Glu Asn Tyr Val
    50                  55                  60
Asn Glu Ile Arg Asn Ser Tyr Tyr Thr His Trp Leu Ser Ala Ala Glu
65                  70                  75                  80
Arg Ile Leu Val Ala Asp Lys Ile Ile Thr Glu Glu Arg Lys His
                85                  90                  95
Arg Val Gln Glu Ile Leu Glu Gly Arg Tyr Thr Asp Arg Lys Pro Ser
            100                 105                 110
Arg Lys Phe Asp Pro Ala Gln Ile Glu Lys Ala Ile Glu Arg Leu His
            115                 120                 125
Glu Pro His Ser Leu Ala Leu Pro Gly Ala Glu Pro Ser Phe Ser Leu
        130                 135                 140
Gly Asp Lys Ile Lys Val Lys Ser Met Asn Pro Leu Glu His Thr Arg
145                 150                 155                 160
Cys Pro Lys Tyr Val Arg Asn Lys Ile Gly Glu Ile Val Thr Tyr His
                165                 170                 175
Gly Cys Gln Ile Tyr Pro Glu Ser Ser Ala Gly Leu Gly Asp Asp
            180                 185                 190
Pro Arg Pro Leu Tyr Thr Val Ala Phe Ser Ala Gln Glu Leu Trp Gly
        195                 200                 205
Asp Asp Gly Asn Gly Lys Asp Val Val Cys Val Asp Leu Trp Glu Pro
    210                 215                 220
Tyr Leu Ile Ser Ala
225

<210> SEQ ID NO 39
```

<211> LENGTH: 229
<212> TYPE: PRT
<213> ORGANISM: Rhodococcus pyridinovorans MS-38

<400> SEQUENCE: 39

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Ile Ser Trp Trp
            35                  40                  45

Asp Lys Ser Arg Phe Phe Arg Glu Ser Met Gly Asn Glu Asn Tyr Val
        50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
                100                 105                 110

Arg Lys Phe Asp Pro Ala Gln Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Thr Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225
```

<210> SEQ ID NO 40
<211> LENGTH: 229
<212> TYPE: PRT
<213> ORGANISM: Nocardia sp JBRs

<400> SEQUENCE: 40

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Ile Ser Trp Trp
            35                  40                  45

Asp Lys Ser Arg Phe Phe Arg Glu Ser Met Gly Asn Glu Asn Tyr Val
        50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
                100                 105                 110
```

```
Arg Lys Phe Asp Pro Ala Glu Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ala Gly Leu Gly Asp Asp
                180                 185                 190

Pro Arg Pro Leu Tyr Thr Val Ala Phe Ser Ala Gln Glu Leu Trp Gly
            195                 200                 205

Asp Asp Gly Asn Gly Lys Asp Val Val Cys Val Asp Leu Trp Glu Pro
        210                 215                 220

Tyr Leu Ile Ser Ala
225

<210> SEQ ID NO 41
<211> LENGTH: 229
<212> TYPE: PRT
<213> ORGANISM: Nocardia YS-2002

<400> SEQUENCE: 41

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
                100                 105                 110

Arg Lys Phe Asp Pro Ala Glu Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ala Gly Leu Gly Asp Asp
                180                 185                 190

Pro Arg Pro Leu Tyr Thr Val Ala Phe Ser Ala Gln Glu Leu Trp Gly
            195                 200                 205

Asp Asp Gly Asn Gly Lys Asp Val Val Cys Val Asp Leu Trp Glu Pro
        210                 215                 220

Tyr Leu Ile Ser Ala
225
```

-continued

<210> SEQ ID NO 42
<211> LENGTH: 229
<212> TYPE: PRT
<213> ORGANISM: Rhodococcus rhodochrous ATCC39384

<400> SEQUENCE: 42

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Met Ser Trp Trp
            35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Asn Pro Ser
                100                 105                 110

Arg Lys Phe Asp Pro Ala Glu Ile Glu Lys Ala Ile Glu Arg Leu His
            115                 120                 125

Glu Pro His Ser Leu Val Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Asn Arg Ile Gly Glu Ile Val Thr Ser His
                165                 170                 175

Gly Cys Gln Ile Tyr Pro Glu Ser Ser Ser Ala Gly Leu Gly Asp Asp
                180                 185                 190

Pro Arg Pro Leu Tyr Thr Val Ala Phe Ser Ala Gln Glu Leu Trp Gly
            195                 200                 205

Asp Asp Gly Asn Gly Lys Asp Val Val Cys Val Asp Leu Trp Glu Pro
    210                 215                 220

Tyr Leu Ile Ser Ala
225

<210> SEQ ID NO 43
<211> LENGTH: 195
<212> TYPE: PRT
<213> ORGANISM: bacterium SP1

<400> SEQUENCE: 43

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
                20                  25                  30

Thr Leu Ser Ile Leu Thr Trp Met His Leu Lys Gly Ile Ser Trp Trp
            35                  40                  45

Asp Lys Pro Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser

```
                    100                 105                 110
Arg Lys Phe Asp Pro Ala Gln Ile Glu Lys Ala Ile Glu Arg Leu His
            115                 120                 125

Glu Pro His Ser Leu Ala Leu Pro Gly Ala Glu Pro Ser Phe Ser Leu
        130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro
        195

<210> SEQ ID NO 44
<211> LENGTH: 166
<212> TYPE: PRT
<213> ORGANISM: bacterium BD2

<400> SEQUENCE: 44

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asp Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Asn Gln Ser Glu Glu Tyr Glu Pro Ala Gly Thr His Thr
145                 150                 155                 160

Val Pro Glu Ile Cys Ala
                165

<210> SEQ ID NO 45
<211> LENGTH: 218
<212> TYPE: PRT
<213> ORGANISM: Comamonas testosteroni

<400> SEQUENCE: 45

Met Asn Gly Ile His Asp Thr Gly Gly Ala His Gly Tyr Gly Pro Val
1               5                   10                  15

Tyr Arg Glu Pro Asn Glu Pro Val Phe Arg Tyr Asp Trp Glu Lys Thr
            20                  25                  30

Val Met Ser Leu Phe Pro Ala Leu Phe Ala Asn Gly Asn Phe Asn Leu
        35                  40                  45

Asp Glu Phe Arg His Gly Ile Glu Arg Met Asn Pro Ile Asp Tyr Leu
```

```
            50                  55                  60
Lys Gly Thr Tyr Tyr Glu His Trp Ile His Ser Ile Glu Thr Leu Leu
 65                  70                  75                  80

Val Glu Lys Gly Val Leu Thr Ala Thr Glu Leu Ala Thr Gly Lys Ala
                 85                  90                  95

Ser Gly Lys Thr Ala Thr Pro Val Leu Thr Pro Ala Ile Val Asp Gly
                100                 105                 110

Leu Leu Ser Thr Gly Ala Ser Ala Ala Arg Glu Glu Gly Ala Arg Ala
                115                 120                 125

Arg Phe Ala Val Gly Asp Lys Val Arg Val Leu Asn Lys Asn Pro Val
130                 135                 140

Gly His Thr Arg Met Pro Arg Tyr Thr Arg Gly Lys Val Gly Thr Val
145                 150                 155                 160

Val Ile Asp His Gly Val Phe Val Thr Pro Asp Thr Ala Ala His Gly
                165                 170                 175

Lys Gly Glu His Pro Gln His Val Tyr Thr Val Ser Phe Thr Ser Val
                180                 185                 190

Glu Leu Trp Gly Gln Asp Ala Ser Ser Pro Lys Asp Thr Ile Arg Val
                195                 200                 205

Asp Leu Trp Asp Asp Tyr Leu Glu Pro Ala
        210                 215

<210> SEQ ID NO 46
<211> LENGTH: 226
<212> TYPE: PRT
<213> ORGANISM: Geobacillus thermoglucosidasius Q6

<400> SEQUENCE: 46

Met Asn Gly Pro His Asp Leu Gly Gly Lys Arg Asp Phe Gly Pro Ile
 1               5                  10                  15

Ile Lys His Asp Gln Glu Pro Leu Phe His Glu Glu Trp Glu Ala Lys
                 20                  25                  30

Val Leu Ala Met His Phe Ala Leu Leu Gly Gln Gly Val Ile Asn Trp
             35                  40                  45

Asp Glu Phe Arg His Gly Ile Glu Arg Met Gly Tyr Val Tyr Tyr Leu
 50                  55                  60

Thr Ser Ser Tyr Tyr Glu His Trp Leu Ala Ser Leu Glu Thr Val Leu
 65                  70                  75                  80

Ala Glu Lys Asn Ile Ile Asn Ser Glu Gln Tyr Arg Lys Arg Ile Arg
                 85                  90                  95

Glu Ile Glu Tyr Gly Met Ser Val Pro Val Ser Glu Lys Pro Glu Leu
                100                 105                 110

Lys Glu Ser Leu Leu Ser Glu Val Ile Tyr Gly Thr Lys Ile Ser Ser
                115                 120                 125

Glu Arg Arg Glu Ser Thr Val Ser Pro Arg Phe Arg Pro Gly Asp Arg
130                 135                 140

Val Arg Val Lys His Phe Tyr Thr Asn Lys His Thr Arg Cys Pro Gln
145                 150                 155                 160

Tyr Val Met Gly Lys Val Gly Val Val Glu Leu Leu His Gly Asn His
                165                 170                 175

Val Phe Pro Asp Ser Asn Ala His Gly Asp Gly Glu Ala Pro Gln Pro
                180                 185                 190

Leu Tyr Asn Val Arg Phe Glu Ala Arg Glu Leu Trp Gly Gly Glu Ala
                195                 200                 205
```

His Glu Lys Asp Ser Leu Asn Leu Asp Leu Trp Asp Ser Tyr Leu Thr
            210                 215                 220

His Ala
225

<210> SEQ ID NO 47
<211> LENGTH: 233
<212> TYPE: PRT
<213> ORGANISM: Psudonocardia thermophila JCM3095

<400> SEQUENCE: 47

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
    115                 120                 125

Ala Ser Arg Glu Val Asp Arg Pro Lys Phe Lys Glu Gly Asp Val
130                 135                 140

Val Arg Phe Ser Thr Ala Ser Pro Lys Gly His Ala Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
    195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 48
<211> LENGTH: 226
<212> TYPE: PRT
<213> ORGANISM: Rhodococcus rhodochrous Cr4

<400> SEQUENCE: 48

Met Asp Gly Ile His Asp Leu Gly Gly Arg Ala Gly Leu Gly Pro Val
1               5                   10                  15

Asn Pro Glu Pro Gly Glu Pro Val Phe His Ser Arg Trp Glu Arg Ser
                20                  25                  30

Val Leu Thr Met Phe Pro Ala Met Ala Leu Gly Ala Phe Asn Leu
            35                  40                  45

Asp Gln Phe Arg Gly Ala Met Glu Gln Ile Pro Pro His Asp Tyr Leu
    50                  55                  60

```
Thr Ser Gln Tyr Tyr Glu His Trp Met His Ala Met Ile His Tyr Gly
 65                  70                  75                  80

Ile Glu Ala Gly Ile Phe Asp Pro Asn Glu Leu Asp Arg Arg Thr Gln
                 85                  90                  95

Tyr Tyr Leu Glu His Pro Asp Glu Asp Pro Leu Arg Gln Asp Pro
            100                 105                 110

Gln Leu Val Glu Thr Ile Ser Gln Leu Ile Met His Gly Ala Asp Tyr
            115                 120                 125

Arg Arg Pro Thr Asp Ala Glu Gly Val Phe Ala Val Gly Asp Lys Val
130                 135                 140

Val Val Arg Ser Asp Ala Ser Pro Asn Thr His Thr Arg Arg Ala Gly
145                 150                 155                 160

Tyr Ile Arg Gly Arg Thr Gly Glu Ile Val Ala Ala His Gly Ala Tyr
                165                 170                 175

Val Phe Pro Asp Thr Asn Ala Val Gly Ala Gly Glu His Pro Glu His
            180                 185                 190

Leu Tyr Thr Val Arg Phe Ser Ala Thr Glu Leu Trp Gly Glu Thr Ala
            195                 200                 205

Thr Ser Asn Ala Val Asn His Ile Asp Val Phe Glu Pro Tyr Leu Leu
210                 215                 220

Pro Ala
225

<210> SEQ ID NO 49
<211> LENGTH: 203
<212> TYPE: PRT
<213> ORGANISM: Rhodococcus M8

<400> SEQUENCE: 49

Met Ser Glu His Val Asn Lys Tyr Thr Glu Tyr Glu Ala Arg Thr Lys
  1               5                  10                  15

Ala Ile Glu Thr Leu Leu Tyr Glu Arg Gly Leu Ile Thr Pro Ala Ala
                 20                  25                  30

Val Asp Arg Val Val Ser Tyr Tyr Glu Asn Glu Ile Gly Pro Met Gly
             35                  40                  45

Gly Ala Lys Val Val Ala Lys Ser Trp Val Asp Pro Glu Tyr Arg Lys
 50                  55                  60

Trp Leu Glu Glu Asp Ala Thr Ala Ala Met Ala Ser Leu Gly Tyr Ala
 65                  70                  75                  80

Gly Glu Gln Ala His Gln Ile Ser Ala Val Phe Asn Asp Ser Gln Thr
                 85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
            115                 120                 125

Val Val Ala Asp Pro Arg Gly Val Leu Lys Arg Asp Phe Gly Phe Asp
130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
            195                 200
```

<210> SEQ ID NO 50
<211> LENGTH: 203
<212> TYPE: PRT
<213> ORGANISM: Rhodococcus ruber TH

<400> SEQUENCE: 50

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200
```

<210> SEQ ID NO 51
<211> LENGTH: 203
<212> TYPE: PRT
<213> ORGANISM: Rhodococcus pyridinovorans MW3

<400> SEQUENCE: 51

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125
```

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
            195                 200

<210> SEQ ID NO 52
<211> LENGTH: 203
<212> TYPE: PRT
<213> ORGANISM: Rhodococcus pyridinovorans S85-2

<400> SEQUENCE: 52

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
            195                 200

<210> SEQ ID NO 53
<211> LENGTH: 203
<212> TYPE: PRT
<213> ORGANISM: Nocardioides sp JBRs

<400> SEQUENCE: 53

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

```
Gly Ala Lys Val Val Ala Lys Ser Trp Val Asp Pro Glu Tyr Arg Lys
        50                  55                  60

Trp Leu Glu Glu Asp Ala Thr Ala Met Ala Ser Leu Gly Tyr Ala
 65                  70                  75                  80

Gly Glu Gln Ala His Gln Ile Ser Ala Val Phe Asn Asp Ser Gln Thr
                85                  90                  95

His His Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
        180                 185                 190

Ser Asn Ala Leu Thr Pro Gln Glu Val Ile Val
        195                 200

<210> SEQ ID NO 54
<211> LENGTH: 203
<212> TYPE: PRT
<213> ORGANISM: Nocardioides sp YS-2002

<400> SEQUENCE: 54

Met Ser Glu His Val Asn Lys Tyr Thr Glu Tyr Glu Ala Arg Thr Lys
 1               5                  10                  15

Ala Ile Glu Thr Leu Leu Tyr Glu Arg Gly Leu Ile Thr Pro Ala Ala
                20                  25                  30

Val Asp Arg Val Val Ser Tyr Tyr Glu Asn Glu Ile Gly Pro Met Gly
            35                  40                  45

Gly Ala Lys Val Val Ala Lys Ser Trp Val Asp Pro Glu Tyr Arg Lys
        50                  55                  60

Trp Leu Glu Glu Asp Ala Thr Ala Met Ala Ser Leu Gly Tyr Ala
 65                  70                  75                  80

Gly Glu Gln Ala His Gln Ile Ser Ala Val Phe Asn Asp Ser Gln Thr
                85                  90                  95

His His Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
        180                 185                 190

Ser Asn Ala Leu Thr Pro Gln Glu Val Ile Val
        195                 200
```

<210> SEQ ID NO 55
<211> LENGTH: 203
<212> TYPE: PRT
<213> ORGANISM: Bacterium BD2

<400> SEQUENCE: 55

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200
```

<210> SEQ ID NO 56
<211> LENGTH: 180
<212> TYPE: PRT
<213> ORGANISM: Bacterium SP1

<400> SEQUENCE: 56

```
Met Ser Glu His Val Asn Lys Tyr Thr Glu Tyr Glu Ala Arg Thr Lys
1               5                   10                  15

Ala Val Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
50                  55                  60

Trp Leu Glu Glu Asp Ala Thr Ala Ala Met Ala Ser Leu Gly Tyr Ala
65                  70                  75                  80

Gly Glu Gln Ala His His Val Val Val Cys Thr Leu Cys Ser Cys Tyr
                85                  90                  95

Pro Trp Pro Val Leu Gly Leu Pro Pro Ala Trp Tyr Lys Ser Met Glu
            100                 105                 110

Tyr Arg Ser Arg Val Val Ala Asp Pro Arg Gly Val Leu Lys Arg Asp
        115                 120                 125

Phe Gly Phe Asp Ile Pro Asp Glu Val Glu Val Arg Val Trp Asp Ser
```

130                 135                 140
Ser Ser Glu Ile Arg Tyr Ile Val Ile Pro Glu Arg Pro Ala Gly Thr
145                 150                 155                 160

Asp Gly Trp Ser Glu Glu Leu Thr Lys Leu Val Ser Arg Asp Ser
                165                 170                 175

Ile Ile Gly Val
            180

<210> SEQ ID NO 57
<211> LENGTH: 203
<212> TYPE: PRT
<213> ORGANISM: Rhodococcus rhodochrous ATCC39484

<400> SEQUENCE: 57

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
                20                  25                  30

Val Asp Arg Val Val Ser Tyr Tyr Glu Asn Glu Ile Gly Pro Met Gly
            35                  40                  45

Gly Ala Lys Val Val Ala Lys Ser Trp Val Asp Pro Glu Tyr Arg Lys
50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 58
<211> LENGTH: 213
<212> TYPE: PRT
<213> ORGANISM: Sinorhizobium medicae WSM419

<400> SEQUENCE: 58

Met Ser Glu His Arg His Gly Pro Gly Glu His Gly His His His
1               5                   10                  15

Asp Asn His Leu Thr Asp Met Glu Ala Arg Val Lys Ala Leu Glu Thr
                20                  25                  30

Val Leu Thr Glu Lys Gly Leu Ile Asp Pro Ala Ala Ile Asp Ala Ile
            35                  40                  45

Val Asp Thr Tyr Glu Thr Lys Val Gly Pro Arg Asn Gly Ala Arg Val
        50                  55                  60

Val Ala Lys Ala Trp Ser Asp Pro Asp Phe Ala Asp Trp Leu Arg Arg

```
            65                  70                  75                  80
Asp Ala Thr Ala Ala Ile Ala Ser Leu Gly Phe Thr Gly Arg Gln Gly
                85                  90                  95

Glu His Met Arg Ala Val Phe Asn Thr Ser Glu Thr His Asn Leu Ile
            100                 105                 110

Val Cys Thr Leu Cys Ser Cys Tyr Pro Trp Ala Val Leu Gly Leu Pro
        115                 120                 125

Pro Val Trp Tyr Lys Ala Pro Pro Tyr Arg Ser Arg Ala Val Ile Asp
    130                 135                 140

Pro Arg Gly Val Leu Ala Glu Phe Gly Leu Asn Leu Pro Ala Glu Lys
145                 150                 155                 160

Lys Ile Arg Val Trp Asp Ser Thr Ala Glu Leu Arg Tyr Leu Val Val
                165                 170                 175

Pro Glu Arg Pro Ala Ala Thr Asp Asp Leu Gly Glu Asp Ala Leu Ala
            180                 185                 190

Lys Leu Val Thr Arg Asp Ser Met Ile Gly Thr Gly Leu Ala Leu Ser
        195                 200                 205

Pro Glu Ala Phe Arg
    210

<210> SEQ ID NO 59
<211> LENGTH: 205
<212> TYPE: PRT
<213> ORGANISM: Pseudonocardia thermophila JCM3095

<400> SEQUENCE: 59

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
        115                 120                 125

Pro Gln Tyr Arg Ser Arg Val Val Arg Glu Pro Arg Gln Leu Leu Lys
    130                 135                 140

Glu Glu Phe Gly Phe Glu Val Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 60
<211> LENGTH: 207
```

```
<212> TYPE: PRT
<213> ORGANISM: Rhodococcus rhodochrous Cr4

<400> SEQUENCE: 60

Met Thr Ala His Asn Pro Val Gln Gly Thr Phe Pro Arg Ser Asn Glu
1               5                   10                  15

Glu Ile Ala Ala Arg Val Lys Ala Met Glu Ala Ile Leu Val Asp Lys
                20                  25                  30

Gly Leu Ile Ser Thr Asp Ala Ile Asp Tyr Met Ser Ser Val Tyr Glu
            35                  40                  45

Asn Glu Val Gly Pro Gln Leu Gly Ala Lys Ile Ala Ala His Ala Trp
    50                  55                  60

Val Asp Pro Glu Phe Lys Gln Arg Leu Leu Ala Asp Ala Thr Gly Ala
65                  70                  75                  80

Cys Lys Glu Met Gly Val Gly Gly Met Gln Gly Glu Glu Met Val Val
                85                  90                  95

Leu Glu Asn Thr Asp Thr Val Asn Asn Met Val Val Cys Thr Leu Cys
                100                 105                 110

Ser Cys Tyr Pro Trp Pro Val Leu Gly Leu Pro Pro Asn Trp Tyr Lys
            115                 120                 125

Tyr Pro Ala Tyr Arg Ala Arg Ala Ala Arg Asp Pro Arg Gly Val Met
    130                 135                 140

Ala Glu Phe Gly Tyr Thr Pro Ala Ser Asp Val Glu Ile Arg Val Trp
145                 150                 155                 160

Asp Ser Ser Ala Glu Leu Arg Tyr Trp Val Leu Pro Gln Arg Pro Ala
                165                 170                 175

Gly Thr Glu Asn Phe Thr Glu Glu Gln Leu Ala Ala Leu Val Thr Arg
            180                 185                 190

Asp Ser Leu Ile Gly Val Ser Val Pro Thr Ala Pro Asn Lys Ala
            195                 200                 205

<210> SEQ ID NO 61
<211> LENGTH: 6
<212> TYPE: PRT
<213> ORGANISM: Rhodococcus

<400> SEQUENCE: 61

Cys Ser Leu Cys Ser Cys
1               5

<210> SEQ ID NO 62
<211> LENGTH: 6
<212> TYPE: PRT
<213> ORGANISM: Rhodococcus J1-H

<400> SEQUENCE: 62

Cys Thr Leu Cys Ser Cys
1               5
```